United States Patent
Mori et al.

(10) Patent No.: US 8,221,990 B2
(45) Date of Patent: Jul. 17, 2012

(54) SCREENING GPR12 RECEPTOR FOR SUBSTANCES HAVING NESFATIN-1-LIKE ACTION, OR WHICH REGULATE NESFATIN-1 ACTION

(75) Inventors: Masatomo Mori, Maebashi (JP); Hiroshi Eguchi, Hino (JP)

(73) Assignees: Teijin Pharma Limited, Tokyo (JP); National University Corporation Gunma University, Gunma (JP)

( * ) Notice: Subject to any disclaimer, the term of this patent is extended or adjusted under 35 U.S.C. 154(b) by 28 days.

(21) Appl. No.: 12/257,351

(22) Filed: Oct. 23, 2008

(65) Prior Publication Data

US 2009/0233325 A1  Sep. 17, 2009

Related U.S. Application Data

(63) Continuation-in-part of application No. 12/098,279, filed on Apr. 4, 2008, now abandoned.

(60) Provisional application No. 60/907,542, filed on Apr. 6, 2007.

(51) Int. Cl.
  *G01N 33/53* (2006.01)
  *G01N 33/567* (2006.01)
  *G01N 33/566* (2006.01)
  *C12Q 1/02* (2006.01)

(52) U.S. Cl. ............................. 435/7.2; 435/29; 436/501

(58) Field of Classification Search ........................ None
See application file for complete search history.

(56) References Cited

U.S. PATENT DOCUMENTS

| 7,795,390 B2 * | 9/2010 | Mori et al. ..................... 530/350 |
| 2002/0182655 A1 | 12/2002 | Kostenis et al. |
| 2003/0096785 A1 | 5/2003 | Stricker-Krongrad et al. |

FOREIGN PATENT DOCUMENTS

WO  01/48483 A2  7/2001

OTHER PUBLICATIONS

Ignatov A et al. J. Neurosci. 23(3):907-914, Feb. 1, 2003.*
Bjursell M, et al. Biochem. Biophys. Res. COmm. 348(2):359-366, 2006.*
Shinsuke Oh-I, S., et al: "Identification of nesfatin-I as a satiety molecule in the hypothalamus" Nature, vol. 443, Oct. 12, 2006, pp. 709-712, XP002493891.
Uhlenbrock K et al: "Sphingosine 1-phosphate is a ligand of the human gpr3, gpr6 and gpr12 family of constitutively active G protein-coupled receptors" Cellular Signalling, Elsevier Science LTD, GB, vol. 14, No. 11, Nov. 1, 2002, pp. 941-953, XP002229984; ISSN: 0898-6568.
Mikael Bjursell, et al: "G protein-coupled receptor 12 deficiency results in dyslipidemia and obesity in mice" Biochemical and Biophysical Research Communications 348 (2006) 359-366.
Yan-Ling Xu, et al: Orphan G protein-coupled receptors and obesity European Journal of Pharmacology 500 (2004) 243-253.
Atanas Ignatov, et al.: Role of the G-Protein-Coupled Receptor GPR12 as High-Affinity Receptor for Spingosylphosphorylcholine and Its Expression and Function in Brain Development, The Journal of Neuroscience, Feb. 1, 2003; 23(3): 907-914.
Cristina Brailoiu G et al: "Nesfatin-1: Distribution and Interaction with a G Protein-Coupled Receptor in the Rat Brain" Endocrinology, Baltimore, MD, US, vol. 148, Oct. 1, 2007, pp. 5088-5094, XP009104888; ISSN 0013-7227.
Becker, O.M. et al; "G protein-coupled receptors: in silico drug discovery in 3D" PNAS, vol. 101, No. 31, Aug. 3, 2004, pp. 11304-11309, XP002493892.

* cited by examiner

*Primary Examiner* — Robert Landsman
(74) *Attorney, Agent, or Firm* — Sughrue Mion, PLLC

(57) ABSTRACT

An object of the present invention is to identify a Nesfatin-1 receptor, and to provide a method for screening or designing a Nesfatin-1-action regulating substance or a Nesfatin-1-like action substance using the Nesfatin-1 receptor.

A method for screening a Nesfatin-1-like action substance comprising steps of making a test substance act on a receptor protein selected from the group consisting of GPR3, GPR6 and GPR12, and of identifying the Nesfatin-1-like action substance based on a change of Nesfatin-1 action.

3 Claims, 5 Drawing Sheets

SEQUENCE LISTING

<160> NUMBER OF SEQ ID NOS: 51

<210> SEQ ID NO 1
<211> LENGTH: 82
<212> TYPE: PRT
<213> ORGANISM: Homo sapiens

<400> SEQUENCE: 1

Val Pro Ile Asp Ile Asp Lys Thr Lys Val Gln Asn Ile His Pro Val
1               5                   10                  15

Glu Ser Ala Lys Ile Glu Pro Pro Asp Thr Gly Leu Tyr Tyr Asp Glu
            20                  25                  30

Tyr Leu Lys Gln Val Ile Asp Val Leu Glu Thr Asp Lys His Phe Arg
        35                  40                  45

Glu Lys Leu Gln Lys Ala Asp Ile Glu Glu Ile Lys Ser Gly Arg Leu
    50                  55                  60

Ser Lys Glu Leu Asp Leu Val Ser His His Val Arg Thr Lys Leu Asp
65                  70                  75                  80

Glu Leu

<210> SEQ ID NO 2
<211> LENGTH: 82
<212> TYPE: PRT
<213> ORGANISM: Mus musculus

<400> SEQUENCE: 2

Val Pro Ile Asp Val Asp Lys Thr Lys Val His Asn Thr Glu Pro Val
1               5                   10                  15

Glu Asn Ala Arg Ile Glu Pro Pro Asp Thr Gly Leu Tyr Tyr Asp Glu
            20                  25                  30

Tyr Leu Lys Gln Val Ile Glu Val Leu Glu Thr Asp Pro His Phe Arg
        35                  40                  45

Glu Lys Leu Gln Lys Ala Asp Ile Glu Glu Ile Arg Ser Gly Arg Leu
    50                  55                  60

Ser Gln Glu Leu Asp Leu Val Ser His Lys Val Arg Thr Arg Leu Asp
65                  70                  75                  80

Glu Leu

<210> SEQ ID NO 3
<211> LENGTH: 82
<212> TYPE: PRT
<213> ORGANISM: Rattus norvegicus

<400> SEQUENCE: 3

Val Pro Ile Asp Val Asp Lys Thr Lys Val His Asn Val Glu Pro Val
1               5                   10                  15

```
Glu Ser Ala Arg Ile Glu Pro Pro Asp Thr Gly Leu Tyr Tyr Asp Glu
         20                  25                  30

Tyr Leu Lys Gln Val Ile Glu Val Leu Glu Thr Asp Pro His Phe Arg
     35                  40                  45

Glu Lys Leu Gln Lys Ala Asp Ile Glu Glu Ile Arg Ser Gly Arg Leu
 50                  55                  60

Ser Gln Glu Leu Asp Leu Val Ser His Lys Val Arg Thr Arg Leu Asp
 65                  70                  75                  80

Glu Leu

<210> SEQ ID NO 4
<211> LENGTH: 246
<212> TYPE: DNA
<213> ORGANISM: Homo sapiens

<400> SEQUENCE: 4
gtgcctattg acatagacaa gacaaaagta caaatatattc accctgtgga aagtgcgaag      60
atagaaccac cagatactgg actttattat gatgaatatc tcaagcaagt gattgatgtg     120
ctggaaacag ataaacactt cagagaaaag ctccagaaag cagacataga ggaaataaag     180
agtgggaggc taagcaaaga actggattta gtaagtcacc atgtgaggac aaaacttgat     240
gaactg                                                                246

<210> SEQ ID NO 5
<211> LENGTH: 246
<212> TYPE: DNA
<213> ORGANISM: Mus musculus

<400> SEQUENCE: 5
gttcctatcg atgtggacaa gaccaaagta cacaacactg agccagtgga aaatgcaagg      60
atagagccac cagatactgg actttattat gatgaataccc tcaagcaagt gattgaagtc     120
ttggaaacag atccacattt cagagaaaag ctccagaaag cagacataga ggagataagg     180
agcgggaggc tgagtcaaga gctggactta gtaagtcaca aagtgaggac gagactggat     240
gagctg                                                                246

<210> SEQ ID NO 6
<211> LENGTH: 246
<212> TYPE: DNA
<213> ORGANISM: Rattus norvegicus

<400> SEQUENCE: 6
gttcctattg atgtggacaa gaccaaagtg cacaacgtcg agccggtgga aagtgcaagg      60
atagaaccgc cagacacggg actttattat gatgaatacc tcaagcaagt gattgaagtc     120
ttggaaacag atccgcattt cagagaaaag ctccagaaag cagacataga ggagataagg     180
agcgggaggc tgagtcaaga gctggactta gtaagtcaca aagtgaggac gagactggat     240
gaactg                                                                246

<210> SEQ ID NO 7
<211> LENGTH: 2485
<212> TYPE: DNA
<213> ORGANISM: Mus musculus
<220> FEATURE:
<221> NAME/KEY: CDS
<222> LOCATION: (509)..(1513)

<400> SEQUENCE: 7
```

```
aagggaacaa taatttgcag accggccaac tgcaatctaa gagagggagt cgcttgctgt        60
tgtaagtctc ctccgccagc cctaacctgc ttaccccgca ttcctcctgt tcatcccgaa       120
aacccggccg tttacaattc tttaggggaa agcataagaa gccgagcccc agggtcaagg       180
gcgcctcggg gaagccacag gatcaaagta ggtcgccaga ctctccggcc gttcgagtgg       240
gtcttcgcat gactgttgca ggcgggcgtc cacggtggcg ggctcccgcc cctcacgcag       300
ctgcgacctg cggggcgcg cgcagcctcg tggggttccc gcggatgcgc gcccggcggg        360
gagcgcggag ggcggagagc cgggcgcgag caccgcagct cacctgccgc gggcgccacc       420
acggacgtgc cacgcgggtg gcccgagcta ttcggcagca ctgaaggagc cacccctcgg       480
ccagggcgtg ccaaggacag gggttaaaa atg aac gaa gac ccg aag gtc aat        532
                                  Met Asn Glu Asp Pro Lys Val Asn
                                   1               5 tta agc ggg ctg cct cgg gac tgt ata gat gcc ggt gct cca gag aac        580
Leu Ser Gly Leu Pro Arg Asp Cys Ile Asp Ala Gly Ala Pro Glu Asn
 10              15                  20 atc tca gcc gct gtc ccc tcc cag ggc tct gtt gcg gag tca gaa ccc        628
Ile Ser Ala Ala Val Pro Ser Gln Gly Ser Val Ala Glu Ser Glu Pro
 25              30                  35              40 gag ctc gtt gtc aac ccc tgg gac att gtc ttg tgc agc tca gga acc        676
Glu Leu Val Val Asn Pro Trp Asp Ile Val Leu Cys Ser Ser Gly Thr
             45                  50                  55 ctc atc tgc tgt gaa aat gcc gtt gtg gtc ctt atc atc ttc cac agc        724
Leu Ile Cys Cys Glu Asn Ala Val Val Val Leu Ile Ile Phe His Ser
             60                  65                  70 ccc agc ctg cga gcc ccc atg ttc cta ctg ata ggc agc ctg gct ctt        772
Pro Ser Leu Arg Ala Pro Met Phe Leu Leu Ile Gly Ser Leu Ala Leu
         75                  80                  85 gca gac ctg ctg gct ggc ctg gga ctc atc atc aat ttt gtt ttt gcg        820
Ala Asp Leu Leu Ala Gly Leu Gly Leu Ile Ile Asn Phe Val Phe Ala
 90              95                  100 tac ctg ctt cag tca gaa gcc acc aag ctg gtc acc atc gga ctc att        868
Tyr Leu Leu Gln Ser Glu Ala Thr Lys Leu Val Thr Ile Gly Leu Ile
105             110                 115                 120 gtc gcc tct ttc tct gcc tct gtc tgc agt ttg ctg gct att act gtg        916
Val Ala Ser Phe Ser Ala Ser Val Cys Ser Leu Leu Ala Ile Thr Val
             125                 130                 135 gac cgc tac ctc tcg cta tat tac gcc ctg acg tac cac tcc gag agg        964
Asp Arg Tyr Leu Ser Leu Tyr Tyr Ala Leu Thr Tyr His Ser Glu Arg
             140                 145                 150 acc gtc acc ttt acc tat gtc atg cta gtg atg ctc tgg gga acc tcc       1012
Thr Val Thr Phe Thr Tyr Val Met Leu Val Met Leu Trp Gly Thr Ser
         155                 160                 165 atc tgc ctg ggg ctg ctg ccc gtc atg ggc tgg aac tgc ttg agg gac       1060
Ile Cys Leu Gly Leu Leu Pro Val Met Gly Trp Asn Cys Leu Arg Asp
     170                 175                 180 gag tcc acc tgc agc gtg gtc aga cct ctc act aag aac aac gct gcc       1108
Glu Ser Thr Cys Ser Val Val Arg Pro Leu Thr Lys Asn Asn Ala Ala
185                 190                 195                 200 atc ctc tcc atc tcc ttc ctc ttc atg ttt gct ctg atg ctt cag ctc       1156
Ile Leu Ser Ile Ser Phe Leu Phe Met Phe Ala Leu Met Leu Gln Leu
             205                 210                 215 tac atc cag att tgt aag att gtg atg agg cac gcc cat cag ata gcc       1204
Tyr Ile Gln Ile Cys Lys Ile Val Met Arg His Ala His Gln Ile Ala
             220                 225                 230 ctg cag cac cac ttc ctg gct aca tcg cac tat gtg act acc cgg aaa       1252
Leu Gln His His Phe Leu Ala Thr Ser His Tyr Val Thr Thr Arg Lys
         235                 240                 245
```

```
ggg gtc tcg acc ctg gct ctc atc cta ggg acc ttt gct gcc tgc tgg      1300
Gly Val Ser Thr Leu Ala Leu Ile Leu Gly Thr Phe Ala Ala Cys Trp
    250                 255                 260 atg cct ttc acc ctc tat tcc ttg atc gcc gat tac acc tac cct tcg      1348
Met Pro Phe Thr Leu Tyr Ser Leu Ile Ala Asp Tyr Thr Tyr Pro Ser
265                 270                 275                 280 atc tat acc tat gcc acc ctg ccc gcc acc tac aat tcc atc atc          1396
Ile Tyr Thr Tyr Ala Thr Leu Pro Ala Thr Tyr Asn Ser Ile Ile
                285                 290                 295 aac cct gtc att tac gct ttc aga aac caa gag atc cag aaa gcc ctc      1444
Asn Pro Val Ile Tyr Ala Phe Arg Asn Gln Glu Ile Gln Lys Ala Leu
                300                 305                 310 tgc ctc att tgc tgt ggg tgc atc cct tcc tcg ctg tct cag aga gct     1492
Cys Leu Ile Cys Cys Gly Cys Ile Pro Ser Ser Leu Ser Gln Arg Ala
            315                 320                 325 cgg tct ccc agc gat gtg tag cagccttctc ctcataggac gctgcctcta         1543
Arg Ser Pro Ser Asp Val
        330 ccaagcgctc ccacctccca gggcggccag tgatttcctt ccttaaattc tttgcactgg    1603 atctcacaag cagaagcaat gacatctttt agacacgtat tgacagtgga aatcatctta   1663 ccagtgtttt ttaaaaaaaa aacaaaacaa aactcgactt ctcggctcag cattctgttg   1723 tttggtttgg gagttaggat tgtttgtttt gtttgcttgt ttgtttgttt ggagggtgta   1783 atgggacctc atgtggccat gaaattatac aaaagtctcg ggattttta acctaggctt    1843 gaaaataaat caaagtttta aggaaactg gagaaggaaa acttttttct gaaggaaata    1903 cttttttttt tttaatcaag gtagatcttc cattctgtat gtatctaaca ggataggagc   1963 tttgccatat aaccaaaata gtttatataa ttacatttgg aagggcttgt gtttatttct   2023 aggaattcag taataagtga ccagtaacag aggcgcgaac tcctttcttt cctttcagca   2083 gtagtgactg ctcttaagaa tcactttgca gtttctctgt gttacagttt ggtatgcatg   2143 gttacctgtg gtagtcagat cactaattgc aatattgcca tgttaaaccc agaattaaaa   2203 gagtcatttt ttcttcaata cagttttga aatatccttt ccaaagtgag tcatgaaaaa    2263 aatgttccca attacatatg agatagcact ggttagattt gtcattgtga ttttaaaac    2323 tctagactgg tggttttcag aaaacaaaag agaaaatatt aacagcatct attgaaagaa   2383 gattttattt attttaata tattctgaga gaataaatgg tgtgatacta ttaagaaata    2443 tacaaacatg acttttcaaa tctctaaaaa aaaaaaaaaa aa                      2485

<210> SEQ ID NO 8
<211> LENGTH: 334
<212> TYPE: PRT
<213> ORGANISM: Mus musculus

<400> SEQUENCE: 8

Met Asn Glu Asp Pro Lys Val Asn Leu Ser Gly Leu Pro Arg Asp Cys
1               5                   10                  15

Ile Asp Ala Gly Ala Pro Glu Asn Ile Ser Ala Ala Val Pro Ser Gln
            20                  25                  30

Gly Ser Val Ala Glu Ser Glu Pro Glu Leu Val Val Asn Pro Trp Asp
        35                  40                  45

Ile Val Leu Cys Ser Ser Gly Thr Leu Ile Cys Cys Glu Asn Ala Val
    50                  55                  60

Val Val Leu Ile Ile Phe His Ser Pro Ser Leu Arg Ala Pro Met Phe
65                  70                  75                  80

Leu Leu Ile Gly Ser Leu Ala Leu Ala Asp Leu Leu Ala Gly Leu Gly
```

```
                        85                  90                  95
Leu Ile Ile Asn Phe Val Phe Ala Tyr Leu Leu Gln Ser Glu Ala Thr
                100                 105                 110

Lys Leu Val Thr Ile Gly Leu Ile Val Ala Ser Phe Ser Ala Ser Val
            115                 120                 125

Cys Ser Leu Leu Ala Ile Thr Val Asp Arg Tyr Leu Ser Leu Tyr Tyr
130                 135                 140

Ala Leu Thr Tyr His Ser Glu Arg Thr Val Thr Phe Thr Tyr Val Met
145                 150                 155                 160

Leu Val Met Leu Trp Gly Thr Ser Ile Cys Leu Gly Leu Leu Pro Val
                165                 170                 175

Met Gly Trp Asn Cys Leu Arg Asp Glu Ser Thr Cys Ser Val Val Arg
            180                 185                 190

Pro Leu Thr Lys Asn Asn Ala Ala Ile Leu Ser Ile Ser Phe Leu Phe
        195                 200                 205

Met Phe Ala Leu Met Leu Gln Leu Tyr Ile Gln Ile Cys Lys Ile Val
    210                 215                 220

Met Arg His Ala His Gln Ile Ala Leu Gln His His Phe Leu Ala Thr
225                 230                 235                 240

Ser His Tyr Val Thr Thr Arg Lys Gly Val Ser Thr Leu Ala Leu Ile
                245                 250                 255

Leu Gly Thr Phe Ala Ala Cys Trp Met Pro Phe Thr Leu Tyr Ser Leu
            260                 265                 270

Ile Ala Asp Tyr Thr Tyr Pro Ser Ile Tyr Thr Tyr Ala Thr Leu Leu
        275                 280                 285

Pro Ala Thr Tyr Asn Ser Ile Ile Asn Pro Val Ile Tyr Ala Phe Arg
    290                 295                 300

Asn Gln Glu Ile Gln Lys Ala Leu Cys Leu Ile Cys Cys Gly Cys Ile
305                 310                 315                 320

Pro Ser Ser Leu Ser Gln Arg Ala Arg Ser Pro Ser Asp Val
                325                 330

<210> SEQ ID NO 9
<211> LENGTH: 1083
<212> TYPE: DNA
<213> ORGANISM: Homo sapiens
<220> FEATURE:
<221> NAME/KEY: CDS
<222> LOCATION: (1)..(1083)

<400> SEQUENCE: 9 atg agc atc caa aag acg tat ctg gag gga gat ttt gtc ttt cct gtg     48
Met Ser Ile Gln Lys Thr Tyr Leu Glu Gly Asp Phe Val Phe Pro Val
1               5                   10                  15 agc agc agc agc ttc cta cgg acc ctg ctg gag ccc cag ctc gga tca     96
Ser Ser Ser Ser Phe Leu Arg Thr Leu Leu Glu Pro Gln Leu Gly Ser
            20                  25                  30 gcc ctt ctg aca gca atg aat gct tcg tgc tgc ctg ccc tct gtt cag    144
Ala Leu Leu Thr Ala Met Asn Ala Ser Cys Cys Leu Pro Ser Val Gln
        35                  40                  45 cca aca ctg cct aat ggc tcg gag cac ctc caa gcc cct ttc ttc agc    192
Pro Thr Leu Pro Asn Gly Ser Glu His Leu Gln Ala Pro Phe Phe Ser
    50                  55                  60 aac cag agc agc agc gcc ttc tgt gag cag gtc ttc atc aag ccc gag    240
Asn Gln Ser Ser Ser Ala Phe Cys Glu Gln Val Phe Ile Lys Pro Glu
65                  70                  75                  80 gtt ttc ctg tct ctg ggc atc gtc agt ctg ctg gaa aac atc ctg gtt    288
Val Phe Leu Ser Leu Gly Ile Val Ser Leu Leu Glu Asn Ile Leu Val
```

```
                85                  90                  95
atc ctg gcc gtg gtc agg aac ggc aac ctg cac tcc ccg atg tac ttc        336
Ile Leu Ala Val Val Arg Asn Gly Asn Leu His Ser Pro Met Tyr Phe
            100                 105                 110 ttt ctc tgc agc ctg gcg gtg gcc gac atg ctg gta agt gtg tcc aat        384
Phe Leu Cys Ser Leu Ala Val Ala Asp Met Leu Val Ser Val Ser Asn
        115                 120                 125 gcc ctg gag acc atc atg atc gcc atc gtc cac agc gac tac ctg acc        432
Ala Leu Glu Thr Ile Met Ile Ala Ile Val His Ser Asp Tyr Leu Thr
130                 135                 140 ttc gag gac cag ttt atc cag cac atg gac aac atc ttc gac tcc atg        480
Phe Glu Asp Gln Phe Ile Gln His Met Asp Asn Ile Phe Asp Ser Met
145                 150                 155                 160 atc tgc atc tcc ctg gtg gcc tcc atc tgc aac ctc ctg gcc atc gcc        528
Ile Cys Ile Ser Leu Val Ala Ser Ile Cys Asn Leu Leu Ala Ile Ala
                165                 170                 175 gtc gac agg tac gtc acc atc ttt tac gcg ctc cgc tac cac agc atc        576
Val Asp Arg Tyr Val Thr Ile Phe Tyr Ala Leu Arg Tyr His Ser Ile
            180                 185                 190 atg acc gtg agg aag gcc ctc acc ttg atc gtg gcc atc tgg gtc tgc        624
Met Thr Val Arg Lys Ala Leu Thr Leu Ile Val Ala Ile Trp Val Cys
        195                 200                 205 tgc ggc gtc tgt ggc gtg gtg ttc atc gtc tac tcg gag agc aaa atg        672
Cys Gly Val Cys Gly Val Val Phe Ile Val Tyr Ser Glu Ser Lys Met
210                 215                 220 gtc att gtg tgc ctc atc acc atg ttc ttc gcc atg atg ctc ctc atg        720
Val Ile Val Cys Leu Ile Thr Met Phe Phe Ala Met Met Leu Leu Met
225                 230                 235                 240 ggc acc ctc tac gtg cac atg ttc ctc ttt gcg cgg ctg cac gtc aag        768
Gly Thr Leu Tyr Val His Met Phe Leu Phe Ala Arg Leu His Val Lys
                245                 250                 255 cgc ata gca gca ctg cca cct gcc gac ggg gtg gcc cca cag caa cac        816
Arg Ile Ala Ala Leu Pro Pro Ala Asp Gly Val Ala Pro Gln Gln His
            260                 265                 270 tca tgc atg aag ggg gca gtc acc atc acc att ctc ctg ggc gtg ttc        864
Ser Cys Met Lys Gly Ala Val Thr Ile Thr Ile Leu Leu Gly Val Phe
        275                 280                 285 atc ttc tgc tgg gcc ccc ttc ttc ctc cac ctg gtc ctc atc atc acc        912
Ile Phe Cys Trp Ala Pro Phe Phe Leu His Leu Val Leu Ile Ile Thr
290                 295                 300 tgc ccc acc aac ccc tac tgc atc tgc tac act gcc cac ttc aac acc        960
Cys Pro Thr Asn Pro Tyr Cys Ile Cys Tyr Thr Ala His Phe Asn Thr
305                 310                 315                 320 tac ctg gtc ctc atc atg tgc aac tcc gtc atc gac cca ctc atc tac       1008
Tyr Leu Val Leu Ile Met Cys Asn Ser Val Ile Asp Pro Leu Ile Tyr
                325                 330                 335 gct ttc cgg agc ctg gaa ttg cgc aac acc ttt agg gag att ctc tgt       1056
Ala Phe Arg Ser Leu Glu Leu Arg Asn Thr Phe Arg Glu Ile Leu Cys
            340                 345                 350 ggc tgc aac ggc atg aac ttg gga tag                                   1083
Gly Cys Asn Gly Met Asn Leu Gly
        355                 360

<210> SEQ ID NO 10
<211> LENGTH: 360
<212> TYPE: PRT
<213> ORGANISM: Homo sapiens

<400> SEQUENCE: 10

Met Ser Ile Gln Lys Thr Tyr Leu Glu Gly Asp Phe Val Phe Pro Val
1               5                   10                  15
```

```
Ser Ser Ser Ser Phe Leu Arg Thr Leu Leu Glu Pro Gln Leu Gly Ser
            20                  25                  30

Ala Leu Leu Thr Ala Met Asn Ala Ser Cys Cys Leu Pro Ser Val Gln
         35                  40                  45

Pro Thr Leu Pro Asn Gly Ser Glu His Leu Gln Ala Pro Phe Phe Ser
     50                  55                  60

Asn Gln Ser Ser Ser Ala Phe Cys Glu Gln Val Phe Ile Lys Pro Glu
65                  70                  75                  80

Val Phe Leu Ser Leu Gly Ile Val Ser Leu Leu Glu Asn Ile Leu Val
                85                  90                  95

Ile Leu Ala Val Val Arg Asn Gly Asn Leu His Ser Pro Met Tyr Phe
                100                 105                 110

Phe Leu Cys Ser Leu Ala Val Ala Asp Met Leu Val Ser Val Ser Asn
            115                 120                 125

Ala Leu Glu Thr Ile Met Ile Ala Ile Val His Ser Asp Tyr Leu Thr
         130                 135                 140

Phe Glu Asp Gln Phe Ile Gln His Met Asp Asn Ile Phe Asp Ser Met
145                 150                 155                 160

Ile Cys Ile Ser Leu Val Ala Ser Ile Cys Asn Leu Leu Ala Ile Ala
                165                 170                 175

Val Asp Arg Tyr Val Thr Ile Phe Tyr Ala Leu Arg Tyr His Ser Ile
            180                 185                 190

Met Thr Val Arg Lys Ala Leu Thr Leu Ile Val Ala Ile Trp Val Cys
         195                 200                 205

Cys Gly Val Cys Gly Val Val Phe Ile Val Tyr Ser Glu Ser Lys Met
210                 215                 220

Val Ile Val Cys Leu Ile Thr Met Phe Phe Ala Met Met Leu Leu Met
225                 230                 235                 240

Gly Thr Leu Tyr Val His Met Phe Leu Phe Ala Arg Leu His Val Lys
                245                 250                 255

Arg Ile Ala Ala Leu Pro Pro Ala Asp Gly Val Ala Pro Gln Gln His
            260                 265                 270

Ser Cys Met Lys Gly Ala Val Thr Ile Thr Ile Leu Leu Gly Val Phe
         275                 280                 285

Ile Phe Cys Trp Ala Pro Phe Phe Leu His Leu Val Leu Ile Ile Thr
     290                 295                 300

Cys Pro Thr Asn Pro Tyr Cys Ile Cys Tyr Thr Ala His Phe Asn Thr
305                 310                 315                 320

Tyr Leu Val Leu Ile Met Cys Asn Ser Val Ile Asp Pro Leu Ile Tyr
                325                 330                 335

Ala Phe Arg Ser Leu Glu Leu Arg Asn Thr Phe Arg Glu Ile Leu Cys
            340                 345                 350

Gly Cys Asn Gly Met Asn Leu Gly
         355                 360

<210> SEQ ID NO 11
<211> LENGTH: 30
<212> TYPE: PRT
<213> ORGANISM: Homo sapiens

<400> SEQUENCE: 11

Pro Asp Thr Gly Leu Tyr Tyr Asp Glu Tyr Leu Lys Gln Val Ile Asp
1               5                   10                  15

Val Leu Glu Thr Asp Lys His Phe Arg Glu Lys Leu Gln Lys
            20                  25                  30
```

<210> SEQ ID NO 12
<211> LENGTH: 30
<212> TYPE: PRT
<213> ORGANISM: Rattus norvegicus

<400> SEQUENCE: 12

Pro Asp Thr Gly Leu Tyr Tyr Asp Glu Tyr Leu Lys Gln Val Ile Glu
1               5                   10                  15

Val Leu Glu Thr Asp Pro His Phe Arg Glu Lys Leu Gln Lys
            20                  25                  30

<210> SEQ ID NO 13
<211> LENGTH: 30
<212> TYPE: PRT
<213> ORGANISM: Mus musculus

<400> SEQUENCE: 13

Pro Asp Thr Gly Leu Tyr Tyr Asp Glu Tyr Leu Lys Gln Val Ile Glu
1               5                   10                  15

Val Leu Glu Thr Asp Pro His Phe Arg Glu Lys Leu Gln Lys
            20                  25                  30

<210> SEQ ID NO 14
<211> LENGTH: 16
<212> TYPE: PRT
<213> ORGANISM: Homo sapiens

<400> SEQUENCE: 14

Pro Asp Thr Gly Leu Tyr Tyr Asp Glu Tyr Leu Lys Gln Val Ile Asp
1               5                   10                  15

<210> SEQ ID NO 15
<211> LENGTH: 14
<212> TYPE: PRT
<213> ORGANISM: Homo sapiens

<400> SEQUENCE: 15

Val Leu Glu Thr Asp Lys His Phe Arg Glu Lys Leu Gln Lys
1               5                   10

<210> SEQ ID NO 16
<211> LENGTH: 10
<212> TYPE: PRT
<213> ORGANISM: Homo sapiens

<400> SEQUENCE: 16

Lys Gln Val Ile Asp Val Leu Glu Thr Asp
1               5                   10

<210> SEQ ID NO 17
<211> LENGTH: 16
<212> TYPE: PRT
<213> ORGANISM: Rattus norvegicus

<400> SEQUENCE: 17

Pro Asp Thr Gly Leu Tyr Tyr Asp Glu Tyr Leu Lys Gln Val Ile Glu
1               5                   10                  15

<210> SEQ ID NO 18
<211> LENGTH: 14
<212> TYPE: PRT
<213> ORGANISM: Rattus norvegicus

<400> SEQUENCE: 18

Val Leu Glu Thr Asp Pro His Phe Arg Glu Lys Leu Gln Lys
1               5                   10

<210> SEQ ID NO 19
<211> LENGTH: 10
<212> TYPE: PRT
<213> ORGANISM: Rattus norvegicus

<400> SEQUENCE: 19

Lys Gln Val Ile Glu Val Leu Glu Thr Asp
1               5                   10

<210> SEQ ID NO 20
<211> LENGTH: 16
<212> TYPE: PRT
<213> ORGANISM: Mus musculus

<400> SEQUENCE: 20

Pro Asp Thr Gly Leu Tyr Tyr Asp Glu Tyr Leu Lys Gln Val Ile Glu
1               5                   10                  15

<210> SEQ ID NO 21
<211> LENGTH: 14
<212> TYPE: PRT
<213> ORGANISM: Mus musculus

<400> SEQUENCE: 21

Val Leu Glu Thr Asp Pro His Phe Arg Glu Lys Leu Gln Lys
1               5                   10

<210> SEQ ID NO 22
<211> LENGTH: 10
<212> TYPE: PRT
<213> ORGANISM: Mus musculus

<400> SEQUENCE: 22

Lys Gln Val Ile Glu Val Leu Glu Thr Asp
1               5                   10

<210> SEQ ID NO 23
<211> LENGTH: 77
<212> TYPE: PRT
<213> ORGANISM: Homo sapiens

<400> SEQUENCE: 23

Val Pro Leu Glu Arg Gly Ala Pro Asn Lys Glu Glu Thr Pro Ala Thr
1               5                   10                  15

Glu Ser Pro Asp Thr Gly Leu Tyr Tyr His Arg Tyr Leu Gln Glu Val
                20                  25                  30

Ile Asp Val Leu Glu Thr Asp Gly His Phe Arg Glu Lys Leu Gln Ala
                35                  40                  45

Ala Asn Ala Glu Asp Ile Lys Ser Gly Lys Leu Ser Arg Glu Leu Asp
            50                  55                  60

Phe Val Ser His His Val Arg Thr Lys Leu Asp Glu Leu
65                  70                  75

<210> SEQ ID NO 24
<211> LENGTH: 77
<212> TYPE: PRT
<213> ORGANISM: Rattus norvegicus

<400> SEQUENCE: 24

Val Pro Val Asp Arg Ala Ala Pro His Gln Glu Asp Asn Gln Ala Thr

```
                  1               5                  10                  15
Glu Thr Pro Asp Thr Gly Leu Tyr Tyr His Arg Tyr Leu Gln Glu Val
                    20                  25                  30

Ile Asn Val Leu Glu Thr Asp Gly His Phe Arg Glu Lys Leu Gln Ala
                35                  40                  45

Ala Asn Ala Glu Asp Ile Lys Ser Gly Lys Leu Ser Gln Glu Leu Asp
            50                  55                  60

Phe Val Ser His Asn Val Arg Thr Lys Leu Asp Glu Leu
65                  70                  75

<210> SEQ ID NO 25
<211> LENGTH: 77
<212> TYPE: PRT
<213> ORGANISM: Mus musculus

<400> SEQUENCE: 25

Val Pro Val Asp Arg Ala Ala Pro Pro Gln Glu Asp Ser Gln Ala Thr
1               5                   10                  15

Glu Thr Pro Asp Thr Gly Leu Tyr Tyr His Arg Tyr Leu Gln Glu Val
                    20                  25                  30

Ile Asn Val Leu Glu Thr Asp Gly His Phe Arg Glu Lys Leu Gln Ala
                35                  40                  45

Ala Asn Ala Glu Asp Ile Lys Ser Gly Lys Leu Ser Gln Glu Leu Asp
            50                  55                  60

Phe Val Ser His Asn Val Arg Thr Lys Leu Asp Glu Leu
65                  70                  75

<210> SEQ ID NO 26
<211> LENGTH: 30
<212> TYPE: PRT
<213> ORGANISM: Homo sapiens

<400> SEQUENCE: 26

Pro Asp Thr Gly Leu Tyr Tyr His Arg Tyr Leu Gln Glu Val Ile Asp
1               5                   10                  15

Val Leu Glu Thr Asp Gly His Phe Arg Glu Lys Leu Gln Ala
                20                  25                  30

<210> SEQ ID NO 27
<211> LENGTH: 30
<212> TYPE: PRT
<213> ORGANISM: Rattus norvegicus

<400> SEQUENCE: 27

Pro Asp Thr Gly Leu Tyr Tyr His Arg Tyr Leu Gln Glu Val Ile Asn
1               5                   10                  15

Val Leu Glu Thr Asp Gly His Phe Arg Glu Lys Leu Gln Ala
                20                  25                  30

<210> SEQ ID NO 28
<211> LENGTH: 30
<212> TYPE: PRT
<213> ORGANISM: Mus musculus

<400> SEQUENCE: 28

Pro Asp Thr Gly Leu Tyr Tyr His Arg Tyr Leu Gln Glu Val Ile Asn
1               5                   10                  15

Val Leu Glu Thr Asp Gly His Phe Arg Glu Lys Leu Gln Ala
                20                  25                  30
```

```
<210> SEQ ID NO 29
<211> LENGTH: 16
<212> TYPE: PRT
<213> ORGANISM: Homo sapiens

<400> SEQUENCE: 29

Pro Asp Thr Gly Leu Tyr Tyr His Arg Tyr Leu Gln Glu Val Ile Asp
1               5                   10                  15

<210> SEQ ID NO 30
<211> LENGTH: 14
<212> TYPE: PRT
<213> ORGANISM: Homo sapiens

<400> SEQUENCE: 30

Val Leu Glu Thr Asp Gly His Phe Arg Glu Lys Leu Gln Ala
1               5                   10

<210> SEQ ID NO 31
<211> LENGTH: 10
<212> TYPE: PRT
<213> ORGANISM: Homo sapiens

<400> SEQUENCE: 31

Gln Glu Val Ile Asp Val Leu Glu Thr Asp
1               5                   10

<210> SEQ ID NO 32
<211> LENGTH: 16
<212> TYPE: PRT
<213> ORGANISM: Rattus norvegicus

<400> SEQUENCE: 32

Pro Asp Thr Gly Leu Tyr Tyr His Arg Tyr Leu Gln Glu Val Ile Asn
1               5                   10                  15

<210> SEQ ID NO 33
<211> LENGTH: 14
<212> TYPE: PRT
<213> ORGANISM: Rattus norvegicus

<400> SEQUENCE: 33

Val Leu Glu Thr Asp Gly His Phe Arg Glu Lys Leu Gln Ala
1               5                   10

<210> SEQ ID NO 34
<211> LENGTH: 10
<212> TYPE: PRT
<213> ORGANISM: Rattus norvegicus

<400> SEQUENCE: 34

Gln Glu Val Ile Asn Val Leu Glu Thr Asp
1               5                   10

<210> SEQ ID NO 35
<211> LENGTH: 16
<212> TYPE: PRT
<213> ORGANISM: Mus musculus

<400> SEQUENCE: 35

Pro Asp Thr Gly Leu Tyr Tyr His Arg Tyr Leu Gln Glu Val Ile Asn
1               5                   10                  15

<210> SEQ ID NO 36
<211> LENGTH: 14
<212> TYPE: PRT
```

<213> ORGANISM: Mus musculus

<400> SEQUENCE: 36

Val Leu Glu Thr Asp Gly His Phe Arg Glu Lys Leu Gln Ala
1               5                   10

<210> SEQ ID NO 37
<211> LENGTH: 10
<212> TYPE: PRT
<213> ORGANISM: Mus musculus

<400> SEQUENCE: 37

Gln Glu Val Ile Asn Val Leu Glu Thr Asp
1               5                   10

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
gcacgctgac cgctctggaa g                                             21

<210> SEQ ID NO 39
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 39
caaatgtgtt aggattctgg tggttca                                       27

<210> SEQ ID NO 40
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 40
ggttccgcgg gtctggttcc gcgtggttct cctatcgatg tggacaagac caa           53

<210> SEQ ID NO 41
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 41
ggttgcggcc gcttacctct tcagctcatc cagtctcg                           38

<210> SEQ ID NO 42
<211> LENGTH: 420
<212> TYPE: PRT
<213> ORGANISM: Homo sapiens

<400> SEQUENCE: 42

Met Arg Trp Arg Thr Ile Leu Leu Gln Tyr Cys Phe Leu Leu Ile Thr
1               5                   10                  15

Cys Leu Leu Thr Ala Leu Glu Ala Val Pro Ile Asp Ile Asp Lys Thr
                20                  25                  30

```
Lys Val Gln Asn Ile His Pro Val Glu Ser Ala Lys Ile Glu Pro Pro
         35                  40                  45

Asp Thr Gly Leu Tyr Tyr Asp Glu Tyr Leu Lys Gln Val Ile Asp Val
 50                  55                  60

Leu Glu Thr Asp Lys His Phe Arg Glu Lys Leu Gln Lys Ala Asp Ile
 65                  70                  75                  80

Glu Glu Ile Lys Ser Gly Arg Leu Ser Lys Glu Leu Asp Leu Val Ser
                 85                  90                  95

His His Val Arg Thr Lys Leu Asp Glu Leu Lys Arg Gln Glu Val Gly
                100                 105                 110

Arg Leu Arg Met Leu Ile Lys Ala Lys Leu Asp Ser Leu Gln Asp Ile
            115                 120                 125

Gly Met Asp His Gln Ala Leu Leu Lys Gln Phe Asp His Leu Asn His
130                 135                 140

Leu Asn Pro Asp Lys Phe Glu Ser Thr Asp Leu Asp Met Leu Ile Lys
145                 150                 155                 160

Ala Ala Thr Ser Asp Leu Glu His Tyr Asp Lys Thr Arg His Glu Glu
                165                 170                 175

Phe Lys Lys Tyr Glu Met Met Lys Glu His Glu Arg Arg Glu Tyr Leu
            180                 185                 190

Lys Thr Leu Asn Glu Glu Lys Arg Lys Glu Glu Ser Lys Phe Glu
            195                 200                 205

Glu Met Lys Lys Lys His Glu Asn His Pro Lys Val Asn His Pro Gly
210                 215                 220

Ser Lys Asp Gln Leu Lys Glu Val Trp Glu Glu Thr Asp Gly Leu Asp
225                 230                 235                 240

Pro Asn Asp Phe Asp Pro Lys Thr Phe Phe Lys Leu His Asp Val Asn
                245                 250                 255

Ser Asp Gly Phe Leu Asp Glu Gln Glu Leu Glu Ala Leu Phe Thr Lys
                260                 265                 270

Glu Leu Glu Lys Val Tyr Asp Pro Lys Asn Glu Glu Asp Asp Met Val
            275                 280                 285

Glu Met Glu Glu Glu Arg Leu Arg Met Arg Glu His Val Met Asn Glu
290                 295                 300

Val Asp Thr Asn Lys Asp Arg Leu Val Thr Leu Glu Glu Phe Leu Lys
305                 310                 315                 320

Ala Thr Glu Lys Lys Glu Phe Leu Glu Pro Asp Ser Trp Glu Thr Leu
                325                 330                 335

Asp Gln Gln Gln Phe Phe Thr Glu Glu Leu Lys Glu Tyr Glu Asn
            340                 345                 350

Ile Ile Ala Leu Gln Glu Asn Glu Leu Lys Lys Lys Ala Asp Glu Leu
            355                 360                 365

Gln Lys Gln Lys Glu Glu Leu Gln Arg Gln His Asp Gln Leu Glu Ala
    370                 375                 380

Gln Lys Leu Glu Tyr His Gln Val Ile Gln Gln Met Glu Gln Lys Lys
385                 390                 395                 400

Leu Gln Gln Gly Ile Pro Pro Ser Gly Pro Ala Gly Glu Leu Lys Phe
                405                 410                 415

Glu Pro His Ile
            420

<210> SEQ ID NO 43
<211> LENGTH: 396
<212> TYPE: PRT
<213> ORGANISM: Homo sapiens
```

<400> SEQUENCE: 43

```
Val Pro Ile Asp Ile Asp Lys Thr Lys Val Gln Asn Ile His Pro Val
1               5                   10                  15
Glu Ser Ala Lys Ile Glu Pro Pro Asp Thr Gly Leu Tyr Tyr Asp Glu
            20                  25                  30
Tyr Leu Lys Gln Val Ile Asp Val Leu Glu Thr Asp Lys His Phe Arg
        35                  40                  45
Glu Lys Leu Gln Lys Ala Asp Ile Glu Glu Ile Lys Ser Gly Arg Leu
    50                  55                  60
Ser Lys Glu Leu Asp Leu Val Ser His Val Arg Thr Lys Leu Asp
65                  70                  75                  80
Glu Leu Lys Arg Gln Glu Val Gly Arg Leu Arg Met Leu Ile Lys Ala
                85                  90                  95
Lys Leu Asp Ser Leu Gln Asp Ile Gly Met Asp His Gln Ala Leu Leu
            100                 105                 110
Lys Gln Phe Asp His Leu Asn His Leu Asn Pro Asp Lys Phe Glu Ser
        115                 120                 125
Thr Asp Leu Asp Met Leu Ile Lys Ala Ala Thr Ser Asp Leu Glu His
    130                 135                 140
Tyr Asp Lys Thr Arg His Glu Glu Phe Lys Lys Tyr Glu Met Met Lys
145                 150                 155                 160
Glu His Glu Arg Arg Glu Tyr Leu Lys Thr Leu Asn Glu Glu Lys Arg
                165                 170                 175
Lys Glu Glu Glu Ser Lys Phe Glu Glu Met Lys Lys Lys His Glu Asn
            180                 185                 190
His Pro Lys Val Asn His Pro Gly Ser Lys Asp Gln Leu Lys Glu Val
        195                 200                 205
Trp Glu Glu Thr Asp Gly Leu Asp Pro Asn Asp Phe Asp Pro Lys Thr
    210                 215                 220
Phe Phe Lys Leu His Asp Val Asn Ser Asp Gly Phe Leu Asp Glu Gln
225                 230                 235                 240
Glu Leu Glu Ala Leu Phe Thr Lys Glu Leu Glu Lys Val Tyr Asp Pro
                245                 250                 255
Lys Asn Glu Glu Asp Asp Met Val Glu Met Glu Glu Glu Arg Leu Arg
            260                 265                 270
Met Arg Glu His Val Met Asn Glu Val Asp Thr Asn Lys Asp Arg Leu
        275                 280                 285
Val Thr Leu Glu Glu Phe Leu Lys Ala Thr Glu Lys Lys Glu Phe Leu
    290                 295                 300
Glu Pro Asp Ser Trp Glu Thr Leu Asp Gln Gln Gln Phe Phe Thr Glu
305                 310                 315                 320
Glu Glu Leu Lys Glu Tyr Glu Asn Ile Ile Ala Leu Gln Glu Asn Glu
                325                 330                 335
Leu Lys Lys Lys Ala Asp Glu Leu Gln Lys Gln Glu Glu Leu Gln
            340                 345                 350
Arg Gln His Asp Gln Leu Glu Ala Gln Lys Leu Glu Tyr His Gln Val
        355                 360                 365
Ile Gln Gln Met Glu Gln Lys Lys Leu Gln Gln Gly Ile Pro Pro Ser
    370                 375                 380
Gly Pro Ala Gly Glu Leu Lys Phe Glu Pro His Ile
385                 390                 395
```

<210> SEQ ID NO 44

<211> LENGTH: 420
<212> TYPE: PRT
<213> ORGANISM: Mus musculus

<400> SEQUENCE: 44

```
Met Arg Trp Arg Ile Ile Gln Val Gln Tyr Cys Phe Leu Leu Val Pro
1               5                   10                  15

Cys Thr Leu Thr Ala Leu Glu Ala Val Pro Ile Asp Val Asp Lys Thr
            20                  25                  30

Lys Val His Asn Thr Glu Pro Val Glu Asn Ala Arg Ile Glu Pro Pro
        35                  40                  45

Asp Thr Gly Leu Tyr Tyr Asp Glu Tyr Leu Lys Gln Val Ile Glu Val
    50                  55                  60

Leu Glu Thr Asp Pro His Phe Arg Glu Lys Leu Gln Lys Ala Asp Ile
65                  70                  75                  80

Glu Glu Ile Arg Ser Gly Arg Leu Ser Gln Glu Leu Asp Leu Val Ser
                85                  90                  95

His Lys Val Arg Thr Arg Leu Asp Glu Leu Lys Arg Gln Glu Val Gly
            100                 105                 110

Arg Leu Arg Met Leu Ile Lys Ala Lys Leu Asp Ala Leu Gln Asp Thr
        115                 120                 125

Gly Met Asn His His Leu Leu Leu Lys Gln Phe Glu His Leu Asn His
    130                 135                 140

Gln Asn Pro Asn Thr Phe Glu Ser Arg Asp Leu Asp Met Leu Ile Lys
145                 150                 155                 160

Ala Ala Thr Ala Asp Leu Glu Gln Tyr Asp Arg Thr Arg His Glu Glu
                165                 170                 175

Phe Lys Lys Tyr Glu Met Met Lys Glu His Glu Arg Arg Glu Tyr Leu
            180                 185                 190

Lys Thr Leu Ser Glu Glu Lys Arg Lys Glu Glu Ser Lys Phe Glu
        195                 200                 205

Glu Met Lys Arg Lys His Glu Asp His Pro Lys Val Asn His Pro Gly
    210                 215                 220

Ser Lys Asp Gln Leu Lys Glu Val Trp Glu Glu Thr Asp Gly Leu Asp
225                 230                 235                 240

Pro Asn Asp Phe Asp Pro Lys Thr Phe Phe Lys Leu His Asp Val Asn
                245                 250                 255

Asn Asp Gly Phe Leu Asp Glu Gln Glu Leu Glu Ala Leu Phe Thr Arg
            260                 265                 270

Glu Leu Glu Lys Val Tyr Asn Pro Gln Asn Ala Glu Asp Asp Met Ile
        275                 280                 285

Glu Met Glu Glu Glu Arg Leu Arg Met Arg Glu His Val Met Ser Glu
    290                 295                 300

Ile Asp Asn Asn Lys Asp Arg Leu Val Thr Leu Glu Glu Phe Leu Arg
305                 310                 315                 320

Ala Thr Glu Lys Lys Glu Phe Leu Glu Pro Asp Ser Trp Glu Thr Leu
                325                 330                 335

Asp Gln Gln Gln Leu Phe Thr Glu Asp Glu Leu Lys Glu Tyr Glu Ser
            340                 345                 350

Ile Ile Ala Ile Gln Glu Asn Glu Leu Lys Lys Arg Ala Glu Glu Leu
        355                 360                 365

Gln Lys Gln Lys Glu Asp Leu Gln Arg Gln His Asp His Leu Glu Ala
    370                 375                 380

Gln Lys Gln Glu Tyr His Gln Ala Val Gln His Leu Glu Gln Lys Lys
385                 390                 395                 400
```

Leu Gln Gln Gly Ile Ala Pro Ser Gly Pro Ala Gly Glu Leu Lys Phe
                405                 410                 415
Glu Pro His Thr
            420

<210> SEQ ID NO 45
<211> LENGTH: 395
<212> TYPE: PRT
<213> ORGANISM: Mus musculus

<400> SEQUENCE: 45

Pro Ile Asp Val Asp Lys Thr Lys Val His Asn Thr Glu Pro Val Glu
1               5                   10                  15
Asn Ala Arg Ile Glu Pro Pro Asp Thr Gly Leu Tyr Tyr Asp Glu Tyr
                20                  25                  30
Leu Lys Gln Val Ile Glu Val Leu Glu Thr Asp Pro His Phe Arg Glu
            35                  40                  45
Lys Leu Gln Lys Ala Asp Ile Glu Glu Ile Arg Ser Gly Arg Leu Ser
50                  55                  60
Gln Glu Leu Asp Leu Val Ser His Lys Val Arg Thr Arg Leu Asp Glu
65                  70                  75                  80
Leu Lys Arg Gln Glu Val Gly Arg Leu Arg Met Leu Ile Lys Ala Lys
                85                  90                  95
Leu Asp Ala Leu Gln Asp Thr Gly Met Asn His His Leu Leu Leu Lys
            100                 105                 110
Gln Phe Glu His Leu Asn His Gln Asn Pro Asn Thr Phe Glu Ser Arg
        115                 120                 125
Asp Leu Asp Met Leu Ile Lys Ala Ala Thr Ala Asp Leu Glu Gln Tyr
130                 135                 140
Asp Arg Thr Arg His Glu Glu Phe Lys Lys Tyr Glu Met Met Lys Glu
145                 150                 155                 160
His Glu Arg Arg Glu Tyr Leu Lys Thr Leu Ser Glu Glu Lys Arg Lys
                165                 170                 175
Glu Glu Glu Ser Lys Phe Glu Glu Met Lys Arg Lys His Glu Asp His
            180                 185                 190
Pro Lys Val Asn His Pro Gly Ser Lys Asp Gln Leu Lys Glu Val Trp
        195                 200                 205
Glu Glu Thr Asp Gly Leu Asp Pro Asn Asp Phe Asp Pro Lys Thr Phe
210                 215                 220
Phe Lys Leu His Asp Val Asn Asn Asp Gly Phe Leu Asp Glu Gln Glu
225                 230                 235                 240
Leu Glu Ala Leu Phe Thr Arg Glu Leu Glu Lys Val Tyr Asn Pro Gln
                245                 250                 255
Asn Ala Glu Asp Asp Met Ile Glu Met Glu Glu Glu Arg Leu Arg Met
            260                 265                 270
Arg Glu His Val Met Ser Glu Ile Asp Asn Asn Lys Asp Arg Leu Val
        275                 280                 285
Thr Leu Glu Glu Phe Leu Arg Ala Thr Glu Lys Lys Glu Phe Leu Glu
290                 295                 300
Pro Asp Ser Trp Glu Thr Leu Asp Gln Gln Leu Phe Thr Glu Asp
305                 310                 315                 320
Glu Leu Lys Glu Tyr Glu Ser Ile Ile Ala Ile Gln Glu Asn Glu Leu
                325                 330                 335
Lys Lys Arg Ala Glu Glu Leu Gln Lys Gln Lys Glu Asp Leu Gln Arg
            340                 345                 350

```
Gln His Asp His Leu Glu Ala Gln Lys Gln Glu Tyr His Gln Ala Val
        355                 360                 365

Gln His Leu Glu Gln Lys Lys Leu Gln Gln Gly Ile Ala Pro Ser Gly
        370                 375                 380

Pro Ala Gly Glu Leu Lys Phe Glu Pro His Thr
385                 390                 395

<210> SEQ ID NO 46
<211> LENGTH: 420
<212> TYPE: PRT
<213> ORGANISM: Rattus norvegicus

<400> SEQUENCE: 46

Met Arg Trp Arg Thr Ile Gln Ala Arg Tyr Cys Phe Leu Leu Val Pro
1               5                   10                  15

Cys Val Leu Thr Ala Leu Glu Ala Val Pro Ile Asp Val Asp Lys Thr
                20                  25                  30

Lys Val His Asn Val Glu Pro Val Glu Ser Ala Arg Ile Glu Pro Pro
            35                  40                  45

Asp Thr Gly Leu Tyr Tyr Asp Glu Tyr Leu Lys Gln Val Ile Glu Val
        50                  55                  60

Leu Glu Thr Asp Pro His Phe Arg Glu Lys Leu Gln Lys Ala Asp Ile
65                  70                  75                  80

Glu Glu Ile Arg Ser Gly Arg Leu Ser Gln Glu Leu Asp Leu Val Ser
                85                  90                  95

His Lys Val Arg Thr Arg Leu Asp Glu Leu Lys Arg Gln Glu Val Gly
            100                 105                 110

Arg Leu Arg Met Leu Ile Lys Ala Lys Leu Asp Ala Leu Gln Asp Thr
        115                 120                 125

Gly Met Asn His His Leu Leu Leu Lys Gln Phe Glu His Leu Asn His
130                 135                 140

Gln Asn Pro Asp Thr Phe Glu Ser Lys Asp Leu Asp Met Leu Ile Lys
145                 150                 155                 160

Ala Ala Thr Ala Asp Leu Glu Gln Tyr Asp Arg Thr Arg His Glu Glu
                165                 170                 175

Phe Lys Lys Tyr Glu Met Met Lys Glu His Glu Arg Arg Glu Tyr Leu
            180                 185                 190

Lys Thr Leu Ser Glu Glu Lys Arg Lys Glu Glu Ala Lys Phe Ala
        195                 200                 205

Glu Met Lys Arg Lys His Glu Asp His Pro Lys Val Asn His Pro Gly
210                 215                 220

Ser Lys Asp Gln Leu Lys Glu Val Trp Glu Glu Thr Asp Gly Leu Asp
225                 230                 235                 240

Pro Asn Asp Phe Asp Pro Lys Thr Phe Phe Lys Leu His Asp Val Asn
                245                 250                 255

Asn Asp Gly Phe Leu Asp Glu Gln Glu Leu Glu Ala Leu Phe Thr Lys
            260                 265                 270

Glu Leu Asp Lys Val Tyr Asn Pro Gln Asn Ala Glu Asp Met Ile
        275                 280                 285

Glu Met Glu Glu Glu Arg Leu Arg Met Arg Glu His Val Met Asn Glu
290                 295                 300

Ile Asp Asn Asn Lys Asp Arg Leu Val Thr Leu Glu Glu Phe Leu Arg
305                 310                 315                 320

Ala Thr Glu Lys Lys Glu Phe Leu Glu Pro Asp Ser Trp Glu Thr Leu
                325                 330                 335
```

Asp Gln Gln Gln Leu Phe Thr Glu Glu Leu Lys Glu Tyr Glu Ser
            340                 345                 350

Ile Ile Ala Ile Gln Glu Ser Glu Leu Lys Lys Ala Asp Glu Leu
            355                 360                 365

Gln Lys Gln Lys Glu Glu Leu Gln Arg Gln His Asp His Leu Glu Ala
370                 375                 380

Gln Lys Gln Glu Tyr Gln Gln Ala Val Gln Gln Leu Glu Gln Lys Lys
385                 390                 395                 400

Phe Gln Gln Gly Ile Ala Pro Ser Gly Pro Ala Gly Glu Leu Lys Phe
            405                 410                 415

Glu Pro His Thr
            420

<210> SEQ ID NO 47
<211> LENGTH: 396
<212> TYPE: PRT
<213> ORGANISM: Rattus norvegicus

<400> SEQUENCE: 47

Val Pro Ile Asp Val Asp Lys Thr Lys Val His Asn Val Glu Pro Val
1               5                   10                  15

Glu Ser Ala Arg Ile Glu Pro Pro Asp Thr Gly Leu Tyr Tyr Asp Glu
            20                  25                  30

Tyr Leu Lys Gln Val Ile Glu Val Leu Glu Thr Asp Pro His Phe Arg
        35                  40                  45

Glu Lys Leu Gln Lys Ala Asp Ile Glu Gly Ile Arg Ser Gly Arg Leu
    50                  55                  60

Ser Gln Glu Leu Asp Leu Val Ser His Lys Val Arg Thr Arg Leu Asp
65                  70                  75                  80

Glu Leu Lys Arg Gln Glu Val Gly Arg Leu Arg Met Leu Ile Lys Ala
                85                  90                  95

Lys Leu Asp Ala Leu Gln Asp Thr Gly Met Asn His His Leu Leu Leu
            100                 105                 110

Lys Gln Phe Glu His Leu Asn His Gln Asn Pro Asp Thr Phe Glu Ser
        115                 120                 125

Lys Asp Leu Asp Met Leu Ile Lys Ala Ala Thr Ala Asp Leu Glu Gln
    130                 135                 140

Tyr Asp Arg Thr Arg His Glu Glu Phe Lys Lys Tyr Glu Met Met Lys
145                 150                 155                 160

Glu His Glu Arg Arg Glu Tyr Leu Lys Thr Leu Ser Glu Glu Lys Arg
                165                 170                 175

Lys Glu Glu Glu Ala Lys Phe Ala Glu Met Lys Arg Lys His Glu Asp
            180                 185                 190

His Pro Lys Val Asn His Pro Gly Ser Lys Asp Gln Leu Lys Glu Val
        195                 200                 205

Trp Glu Glu Thr Asp Gly Leu Asp Pro Asn Asp Phe Asp Pro Lys Thr
    210                 215                 220

Phe Phe Lys Leu His Asp Val Asn Asn Asp Gly Phe Leu Asp Glu Gln
225                 230                 235                 240

Glu Leu Glu Ala Leu Phe Thr Lys Glu Leu Asp Lys Val Tyr Asn Pro
                245                 250                 255

Gln Asn Ala Glu Asp Asp Met Ile Glu Met Glu Glu Glu Arg Leu Arg
            260                 265                 270

Met Arg Glu His Val Met Asn Glu Ile Asp Asn Asn Lys Asp Arg Leu
        275                 280                 285

```
Val Thr Leu Glu Glu Phe Leu Arg Ala Thr Glu Lys Lys Glu Phe Leu
    290                 295                 300

Glu Pro Asp Ser Trp Glu Thr Leu Asp Gln Gln Gln Leu Phe Thr Glu
305                 310                 315                 320

Glu Glu Leu Lys Glu Tyr Glu Ser Ile Ile Ala Ile Gln Glu Ser Glu
                325                 330                 335

Leu Lys Lys Lys Ala Asp Glu Leu Gln Lys Gln Lys Glu Glu Leu Gln
            340                 345                 350

Arg Gln His Asp His Leu Glu Ala Gln Lys Gln Glu Tyr Gln Gln Ala
        355                 360                 365

Val Gln Gln Leu Glu Gln Lys Lys Phe Gln Gln Gly Ile Ala Pro Ser
    370                 375                 380

Gly Pro Ala Gly Glu Leu Lys Phe Glu Pro His Thr
385                 390                 395

<210> SEQ ID NO 48
<211> LENGTH: 330
<212> TYPE: PRT
<213> ORGANISM: Mus musculus

<400> SEQUENCE: 48

Met Met Trp Gly Ala Gly Ser Ser Met Ala Trp Phe Ser Ala Gly Ser
1               5                   10                  15

Gly Ser Val Asn Val Ser Ser Val Asp Pro Val Glu Glu Pro Thr Gly
            20                  25                  30

Pro Ala Thr Leu Leu Pro Ser Pro Arg Ala Trp Asp Val Val Leu Cys
        35                  40                  45

Ile Ser Gly Thr Leu Val Ser Cys Glu Asn Ala Leu Val Val Ala Ile
    50                  55                  60

Ile Val Gly Thr Pro Ala Phe Arg Ala Pro Met Phe Leu Leu Val Gly
65                  70                  75                  80

Ser Leu Ala Val Ala Asp Leu Leu Ala Gly Leu Gly Leu Val Leu His
            85                  90                  95

Phe Ala Ala Asp Phe Cys Ile Gly Ser Pro Glu Met Ser Leu Met Leu
        100                 105                 110

Val Gly Val Leu Ala Met Ala Phe Thr Ala Ser Ile Gly Ser Leu Leu
    115                 120                 125

Ala Ile Thr Val Asp Arg Tyr Leu Ser Leu Tyr Asn Ala Leu Thr Tyr
130                 135                 140

Tyr Ser Glu Thr Thr Val Thr Arg Thr Tyr Val Met Leu Ala Leu Val
145                 150                 155                 160

Trp Val Gly Ala Leu Gly Leu Gly Leu Val Pro Val Leu Ala Trp Asn
            165                 170                 175

Cys Arg Asp Gly Leu Thr Thr Cys Gly Val Val Tyr Pro Leu Ser Lys
        180                 185                 190

Asn His Leu Val Val Leu Ala Ile Ala Phe Phe Met Val Phe Gly Ile
    195                 200                 205

Met Leu Gln Leu Tyr Ala Gln Ile Cys Arg Ile Val Cys Arg His Ala
    210                 215                 220

Gln Gln Ile Ala Leu Gln Arg His Leu Leu Pro Ala Ser His Tyr Val
225                 230                 235                 240

Ala Thr Arg Lys Gly Ile Ala Thr Leu Ala Val Val Leu Gly Ala Phe
            245                 250                 255

Ala Ala Cys Trp Leu Pro Phe Thr Val Tyr Cys Leu Leu Gly Asp Ala
        260                 265                 270
```

```
Asp Ser Pro Arg Leu Tyr Thr Tyr Leu Thr Leu Leu Pro Ala Thr Tyr
            275                 280                 285

Asn Ser Met Ile Asn Pro Val Ile Tyr Ala Phe Arg Asn Gln Asp Val
            290                 295                 300

Gln Lys Val Leu Trp Ala Ile Cys Cys Cys Ser Thr Ser Lys Ile
305                 310                 315                 320

Pro Phe Arg Ser Arg Ser Pro Ser Asp Val
            325                 330

<210> SEQ ID NO 49
<211> LENGTH: 363
<212> TYPE: PRT
<213> ORGANISM: Mus musculus

<400> SEQUENCE: 49

Met Asn Ala Ser Ala Ala Ala Leu Asn Glu Ser Gln Val Val Ala Val
1               5                   10                  15

Ala Ala Glu Gly Ala Ala Ala Ala Thr Ala Ala Gly Ala Pro Asp
            20                  25                  30

Thr Gly Glu Trp Gly Pro Ala Ala Ser Ala Ala Leu Gly Gly Gly
            35                  40                  45

Gly Gly Pro Asn Gly Ser Leu Glu Leu Ser Ser Gln Leu Pro Ala Gly
        50                  55                  60

Pro Ser Gly Leu Leu Leu Ser Ala Val Asn Pro Trp Asp Val Leu Leu
65                  70                  75                  80

Cys Val Ser Gly Thr Val Ile Ala Gly Glu Asn Ala Leu Val Val Ala
                85                  90                  95

Leu Ile Ala Ser Thr Pro Ala Leu Arg Thr Pro Met Phe Val Leu Val
            100                 105                 110

Gly Ser Leu Ala Thr Ala Asp Leu Leu Ala Gly Cys Gly Leu Ile Leu
        115                 120                 125

His Phe Val Phe Gln Tyr Val Val Pro Ser Glu Thr Val Ser Leu Leu
    130                 135                 140

Met Val Gly Phe Leu Val Ala Ser Phe Ala Ala Ser Val Ser Ser Leu
145                 150                 155                 160

Leu Ala Ile Thr Val Asp Arg Tyr Leu Ser Leu Tyr Asn Ala Leu Thr
                165                 170                 175

Tyr Tyr Ser Arg Arg Thr Leu Leu Gly Val His Leu Leu Leu Ala Ala
            180                 185                 190

Thr Trp Thr Val Ser Leu Gly Leu Gly Leu Leu Pro Val Leu Gly Trp
        195                 200                 205

Asn Cys Leu Ala Asp Arg Thr Ser Cys Ser Val Val Arg Pro Leu Thr
    210                 215                 220

Arg Ser His Val Ala Leu Leu Ser Thr Ser Phe Phe Val Val Phe Gly
225                 230                 235                 240

Ile Met Leu His Leu Tyr Val Arg Ile Cys Gln Val Val Trp Arg His
                245                 250                 255

Ala His Gln Ile Ala Leu Gln Gln His Cys Leu Ala Pro Pro His Leu
            260                 265                 270

Ala Ala Thr Arg Lys Gly Val Gly Thr Leu Ala Val Val Leu Gly Thr
        275                 280                 285

Phe Gly Ala Ser Trp Leu Pro Phe Ala Ile Tyr Cys Val Val Gly Ser
    290                 295                 300

Gln Glu Asp Pro Ala Ile Tyr Thr Tyr Ala Thr Leu Leu Pro Ala Thr
305                 310                 315                 320
```

```
Tyr Asn Ser Met Ile Asn Pro Ile Ile Tyr Ala Phe Arg Asn Gln Glu
                325                 330                 335

Ile Gln Arg Ala Leu Trp Leu Leu Phe Cys Gly Cys Phe Gln Ser Lys
                340                 345                 350

Val Pro Phe Arg Ser Arg Ser Pro Ser Glu Val
                355                 360

<210> SEQ ID NO 50
<211> LENGTH: 30
<212> TYPE: PRT
<213> ORGANISM: Artificial Sequence
<220> FEATURE:
<223> OTHER INFORMATION: Synthetic M30_Ag-A peptide

<400> SEQUENCE: 50

Pro Asp Thr Gly Leu Tyr Tyr Asp Glu Tyr Ala Lys Ala Ala Ala Ala
1               5                   10                  15

Ala Leu Glu Thr Asp Lys His Phe Arg Glu Lys Leu Gln Lys
                20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic M30_MSH-A peptide

<400> SEQUENCE: 51

Pro Asp Thr Gly Leu Tyr Tyr Asp Glu Tyr Leu Lys Gln Val Ile Asp
1               5                   10                  15

Val Leu Glu Thr Asp Ala Ala Ala Ala Glu Lys Leu Gln Lys
                20                  25                  30
```

SCREENING GPR12 RECEPTOR FOR SUBSTANCES HAVING NESFATIN-1-LIKE ACTION, OR WHICH REGULATE NESFATIN-1 ACTION

This is a Continuation-In-Part Application of application Ser. No. 12/098,279 filed Apr. 4, 2008, which claims benefit of Provisional Application No. 60/907,542, filed Apr. 6, 2007, the disclosure of each of which is incorporated herein by reference in its entirety.

TECHNICAL FIELD

The present invention relates to a method for screening a Nesfatin-1-action regulating substance or a Nesfatin-1-like action substance using GPR3, GPR6 or GPR12 that was identified for the first time according to the present invention.

BACKGROUND ART

Obesity is a state having excessive body weight (especially, white adipose tissues), and in general, classified by Body Mass Index (BMI)$\geq 25$ kg/m$^2$ and further classified by a body fat percentage of 25% or more for adult males and 30% or more for adult females. In these days of the dietary habit loaded with high-fat foods and the lack of exercise, the percentage of people classified into obese tends to increase. The results of National Nutrition Survey by the Ministry of Health, Labour and Welfare in 2000 indicate that males classified into the obese have definitely increased in comparison with that in the last decade and two decades, and around 30% of the males from 40 to 69 years old are classified into the obese. Further, in females, around 30% of the females from 60 to 69 years old are also classified into the obese.

Currently, health disorder (capable of being) associated with obesity other than the obesity itself is clinically a large issue, and forms a medical reason for the prevention or treatment of obesity. The Japan Society for the Study of Obesity defines adiposis as "a pathological condition complicating health disorder that is caused by or associated with obesity, or medically requiring weight reduction when the complication is clinically predicted" and advocates to treat it as a disease. In "health disorder" herein described, in addition to type 2 diabetes mellitus and impaired glucose tolerance, hypertension, hyperlipemia, hyperuricemia, fatty liver, cardiovascular/cerebrovascular disease, sleep apnea syndrome, orthopedic disease such as osteoarthritis and the like, menstrual disorder and others are included (Yuji Matsuzawa, Nippon-Rinsho, Nippon Rinsho Co., Ltd., "Obesity" extra No. 6, Vol. 61, p5-8, Jul. 28, 2003). In addition, it is reported that as a disease caused by obesity, malignant tumors are mentioned, and obesity is a risk factor for the onset of especially breast cancer, uterus cancer, colon cancer, kidney cancer, esophagus cancer, pancreas cancer, hepatic cancer and gallbladder cancer (Yuji Matsuzawa, Nippon-Rinsho, Nippon Rinsho Co., Ltd., "Obesity" extra No. 6, Vol. 61, p5-8, Jul. 28, 2003; Abu-Abid et al., Journal of medicine (MSA), Vol. 33, No. 1-4, p73-86, Jan. 1, 2002; Nair et al., Hepatology (MSA), Vol. 36, No. 1, p150-155, Jul. 1, 2002). Further, in recent years, a combined risk syndrome that is referred to as a metabolic syndrome and increases the risk of an arteriosclerotic disease (myocardial infarction, cerebral infarction and the like) has been proposed and has drawn the attention for the fact that 30% in total mortality is caused by cerebral vascular disorder and vascular disorder in Japan. Therefore, the diagnostic criteria were established jointly by the Japan Society for the Study of Obesity, the Japan Atherosclerosis Society, the Japan Diabetes Society, the Japanese Society of Hypertension, the Japanese Circulation Society, the Japanese Society of Nephrology, the Japanese Society on Thrombosis and Hemostasis, and the Japanese Society of Internal Medicine and published at the press conference in the Japanese Society of Internal Medicine on 8 Apr. 2005. According to the diagnostic criteria, a metabolic syndrome is diagnosed in the case of having two or more risks among the risks of impaired serum lipid (having either or both a triglyceride level of 150 mg/dL or more and/or an HDL cholesterol level of less than 40 mg/dL), high blood pressure (having either or both a systolic blood pressure of 130 mmHg or more and/or a diastolic blood pressure of 85 mmHg) and high blood sugar (a fasting blood sugar level of 110 mg/dL or more), in addition to having a waist circumference of 85 cm or more for males and 90 cm or more for females, while setting the visceral obesity (visceral fat accumulation) in the center of the risks (Journal of Japanese Society of Internal Medicine, Exploratory Committee for Diagnostic Criteria of Metabolic Syndrome, Vol. 94, April issue in 2005, p794-809). There is also a report that, when the diagnostic criteria are applied, among the adult males who had a complete medical checkup, while 61 males (21%) were diagnosed with adipositas, 27 males (9%) were diagnosed with metabolic syndrome and even 9 males (3%) were diagnosed with metabolic syndrome without being included in adiposis (Kazuo Takahashi, Yasushi Saito, Igaku no Ayumi, Vol. 213, No. 6, p549-554, 2005).

As opposed to the obesity, excessive weight loss (what is called "skinny") and decreased food intake (what is called "decreased appetite") become a problem as a factor of easy infection caused by reduced-biological defense (immune) response, hematopoietic disorder, amenorrhea or irregular menstruation, infertility, psychical disorder, peripheral nerve paralysis, hypotension, osteoporosis and the like. In general, when the BMI is <18.5 kg/m$^2$, or the body fat percentage is 10% or less for males and 15% or less for females, the males/females are classified into "skinny". In the National Nutrition Survey by the Ministry of Health, Labour and Welfare in 2000, the ratio of the females having BMI <18.5 kg/m$^2$ has steadily increased between 20 and 39 years old during the last decade and two decades, and around 24% of the females between 20 and 29 years old are classified into "skinny". This may be caused in young females by intentionally regulating the amount of food intake with a concern for their body shapes. However, in the case of anorexia nervosa (anorexia) and the like among the food intake abnormalities of central origin that occur frequently in this age group, the appetite itself is significantly decreased, and the nutritional status is compromised, as a result, the general debility may cause death. Further, as a disease causing a decrease of appetite and including the concept that is conventionally referred to as descensus ventriculi, gastric atony and neurotic gastritis, there is a disease referred to as "Functional dyspepsia", and the disease is said to exhibit a symptom such as an early satiety sensation after eating, a loss of appetite and the like (Talley et al., Gut (England), Vol. 45, Suppl. 2, p1137-1142, 1999). Furthermore, a factor causing a decreased appetite is exemplified by a cancer, an inflammatory disease, a decline in the function of pituitary gland, thyroid gland, adrenal gland and the like, after surgery, an extreme stress, and others. Under such conditions, by a decreased appetite persisting for a long time, wasting of the body is brought about.

In these circumstances, biological factors regulating food intake are recently actively studied and the relation between a factor such as leptin, adiponectin, ghrelin and the like and the food intake regulation is also studied. In recent years, as a substance associated with food intake and obesity, Nesfatin-1 is reported (Oh-I S. et al., Nature, 443(7112):709-12, 2006), and which is expected as a novel factor involved in the food intake regulation and/or body weight regulation.

A receptor of a certain factor is useful in search for a substance having action similar to such factor or a substance regulating the action of such factor, and is frequently tried to be isolated. However, isolation of the receptor is usually difficult, since the interaction between factor and receptor differs depending on the type of the cells on which such factor acts and the environment in the tissue where the cells are placed. Further, even when the factor has similar action, the factor does not always have a similar receptor structure, and therefore the receptor structure is extremely difficult to be predicted from the factor action.

For example, for leptin that is a biological factor regulating food take, the presence of its receptor is known, but the receptor is a single-transmembrane receptor and known to have a similar structure to that of gp130 that is a signal transduction molecule common to a cytokine receptor such as IL-6, G-CSF, LIF and the like. On the other hand, a receptor of Nesfatin-1 had not been reported yet, and the elucidation has been expected.

A G-protein-coupled receptor (hereinafter, abbreviated as "GPCR") refers to as a receptor group that couples to G proteins to conduct signal transduction, and has a characteristic common structure in which such receptor passes through cell membrane 7 times. In such GPCR, various responses such as hormone, neurotransmitter substances, sensory stimuli and the like are known over the wide range. Among them, in several GPCRs, the relationship with obesity has been reported (Xu et al., European Journal of Pharmacology 500: 243-253, 2004).

In Bjursell M et al., Biochemical and Biophysical Research Communication, 348(2): 359-366, 2006, it is reported that in a GPCR12 (hereinafter, also referred to as GPR12)-KO mouse, the weight gain, the white adipose increase and the like were exhibited, but the food intake was not affected at all, and it is suggested that GPR12 may be involved in a low-energy consumption. Further, this GPR12 is known to form a family with GPR3 and GPR6. In Non-Patent Uhlenbrock K et al., Cellular Signaling, 14(11): 941-953, 2002, it is reported that sphingosine 1-phosphate (hereinafter, abbreviated as "S1P") is an endogenous ligand of GPR12. In Ignatov A et al., The Journal of Neuroscience, 23(3): 907-914, 2003, it is reported that sphingosylphosphorylcholine (hereinafter, abbreviated as "SPC") is an endogenous ligand of GPR12.

DISCLOSURE OF THE INVENTION

An object to be solved by the present invention is to identify the unknown Nesfatin-1 receptor, and using the Nesfatin-1 receptor, to provide a method for screening or designing a substance regulating Nesfatin-1-action or a substance having Nesfatin-1-like action.

The present inventors identified GPR12 as a Nesfatin-1 receptor in which signal transduction is induced by Nesfatin-1 by screening GPCR that expresses in brain as a candidate receptor, and thus completed the present invention based on these findings.

That is, the present invention relates to the following.
(1) A method for screening a Nesfatin-1-like action substance comprising steps of:
    making a test substance act on a receptor protein selected from the group consisting of GPR3, GPR6 and GPR12; and
    identifying the Nesfatin-1-like action substance based on a change of Nesfatin-1 action.

(2) The screening method according to (1), wherein the receptor protein is GPR12.
(3) The screening method according to (1) or (2), wherein the test substance is a peptide or a peptide analog obtained by modifying a peptide having the amino acid sequence represented by any of SEQ ID NOs: 1 to 3 or 11 to 37.
(4) The screening method according to any one of (1) to (3), wherein the step of making a test substance act on a receptor protein is a step of making the test substance act on cells or non-human animal that express the receptor protein.
(5) A method for screening a Nesfatin-1-action regulating substance comprising steps of:
    making a test substance act on a coexisting system of Nesfatin-1 and a receptor protein selected from the group consisting of GPR3, GPR6 and GPR12; and
    identifying the Nesfatin-1-action regulating substance based on a change of Nesfatin-1 action.
(6) The screening method according to (5), wherein the receptor protein is GPR12.
(7) The screening method according to (5) or (6), wherein the step of making a test substance act on a coexisting system of Nesfatin-1 and the receptor protein is a step of making the test substance act on Nesfatin-1, and cells or non-human animal that express the receptor protein.
(8) A method for screening in silico or designing a Nesfatin-1-action regulating substance or a Nesfatin-1-like action substance based on a Nesfatin-1 receptor structure or a ligand structure, wherein the Nesfatin-1 receptor structure is obtained by a simulation based on a known structure information of GPR3, GPR6 or GPR12.

According to the present invention, a method for screening a Nesfatin-1-action regulating substance or a Nesfatin-1-like action substance in vitro or in silico is provided.

Further, the present invention provides a method for screening factors associated with food intake regulation and/or body weight regulation, especially, a therapeutic agent of a disease such as obesity syndrome, eating disorder, dysbolism, diabetes mellitus and the like.

BRIEF DESCRIPTION OF THE DRAWINGS

FIG. 4A is an image of western blotting of CREB and phosphorylated CREB (p-CREB) in proteins extracted with time from the CHO-K1 and CHO-K1-GPR12 cells that were brought into contact with Nesfatin-1M30 (Mid-segment) at a concentration of $10^{-9}$ M. FIG. 4B is an image of western blotting of CREB and p-CREB in proteins extracted from the CHO-K1-GPR12 cells that were brought into contact with Nesfatin-1M30 Mid-segment) at a concentration of $10^{-12}$ M, $10^{-11}$ M, $10^{-10}$ M, $10^{-9}$ M and 0 M for 15 minutes.

FIG. 5A is a bar graph showing the results of luciferase activities when Nesfatin-M30 (Mid-segment), M30_Ag-A and M30_MSH-A each at a concentration of $10^{-10}$ M were brought into contact with the NB41A3 cells transfected with a reporter plasmid (pCRE-Luc). Vehicle shows the results in the NB41A3 cells transfected with pCRE-Luc, where the cells were not brought into contact with a test substance. FIG. 5B is a bar graph showing the results of luciferase activities when the NB41A3 cells transfected with a reporter plasmid (pCRE-Luc) were brought into contact with M30_Ag-A at a concentration of $10^{-8}$ M, $10^{-9}$ M, $10^{-10}$M, $10^{-11}$ $^{M,}$ $10^{-12}$ M, and 0 M. FIG. 5C is a bar graph showing the results of luciferase activities when the NB41A3 cells transfected with a reporter plasmid (pCRE-Luc) were brought into contact with M30_MSH-A at a concentration of $10^{-8}$ M, $10^{-9}$ M, $10^{-10}$ M, $10^{-11}$ M, $10^{-12}$ M, and 0 M.

BEST MODE FOR CARRYING OUT THE INVENTION

Figure 1:
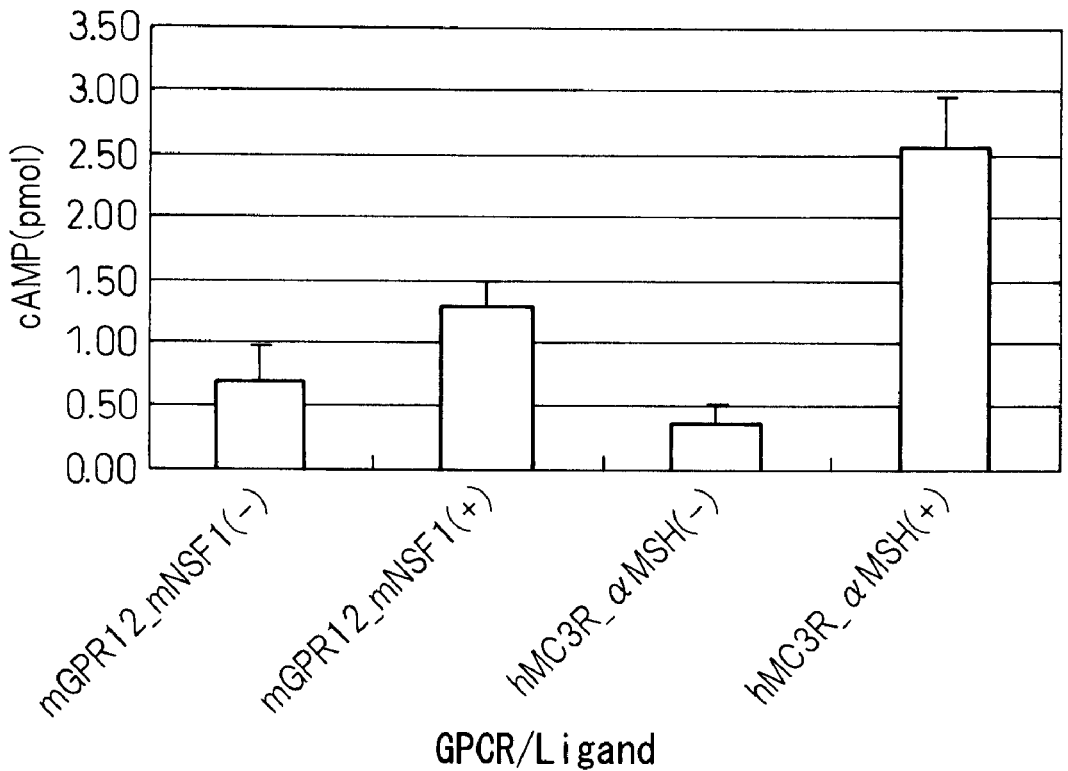
FIG. 1 is a bar graph showing the results comparing the cAMP production level in the absence of Forskolin for cGPR12-transiently expressing HeLa cells and hMC3R-transiently expressing HeLa cells. mGPR12_mNSF1(−) represents mGPR12-transiently expressing HeLa cells without mNSF1 addition, and mGPR12_mNSF1(+) represents mGPR12-expressing cells with mNSF1 addition. As a positive control, hMCR$_3$R_αMSH(−) represents hMC3R-transiently expressing HeLa cells without αMSH addition, and hMCR$_3$R_αMSH(+) represents hMC3R-transiently expressing HeLa cells with αMSH addition. The number of N is 3 (n=2 for hMC3R). SD is shown by a bar.

<A method for screening a Nesfatin-1-Action regulating substance>

The present invention relates to a method for screening a Nesfatin-1-action regulating substance including a step of making a test substance act on a coexisting system of Nesfatin-1 and a receptor protein selected from the group consisting of GPR3, GPR6 and GPR12 and a step of identifying the Nesfatin-1-action regulating substance based on a change of Nesfatin-1 action.

In the present invention, "Nesfatin-1" is a polypeptide having an activity for suppressing food intake and/or body weight gain, represented by any of SEQ ID NOs: 1 to 3. Nesfatin-1 is considered to exhibit an activity for suppressing food intake and/or body weight gain by splicing out from NESFATIN/NEFA using a cleavage enzyme such as a prohormone convertase in vivo, and the like (Oh-I S. et al., Nature, 443(7112): 709-12, 2006).

Such Nesfatin-1 is obtained by cleaving a NESFATIN polypeptide having the amino sequence represented by any of SEQ ID NOs: 42 to 47 using a prohormone convertase, and then purifying using reversed phase chromatography and the like or conducting a step of binding and release to an antibody directed against a Nesfatin-1 polypeptide. Further, a recombinant Nesfatin-1 is obtained as described in Example 1.

GPR12 is a receptor protein for which its function as a Nesfatin-1 receptor has been revealed for the first time in the present invention. Specifically, GPR12 is, for example, a protein having the amino acid sequence represented by SEQ ID NO: 7 or 8. Further, a protein having the amino acid sequence represented by SEQ ID NO: 7 or 8 is a mouse-derived GPR12, but GPR12 functioning as "a Nesfatin-1 receptor" herein includes GPR12s derived from human, rat and others, and their origin is not particularly limited provided that the GPR12 is a protein referred to GPR12.

Since Nesfatin-1 does not show strong homology with a known biological factor having a food intake- and/or body weight-regulating activity, especially a peptide hormone, it was impossible to presume the structure and the like of a Nesfatin-1 receptor from the information used conventionally on the receptor for the biological factor. Therefore, as described in detail in Examples 2 and 3, the present inventors selected 33 types of GPCR based on various hypotheses, obtained the GPCR genes, prepared the cells expressing each GPCR, and found for the first time that GPR12 was a Nesfatin-1 receptor by analyzing the reactivity with Nesfatin-1 under various conditions. Further, as described in Background Art, a ligand of GPR12 was considered to be a substance such as S1P, SPC and the like, and therefore there was no information leading to a prediction that GPR12 was a receptor of the ligand of the peptide containing Nesfatin-1. In addition, it is known to exhibit an activity for suppressing food intake in an animal when Nesfatin-1 was administered to the animal, while it is reported that the food intake was not suppressed in a knockout mouse of GPR12 (Bjursell M et al., BBRC, 348(2):359-66, 2006). Even at this point, it was unexpected that GPR12 was a Nesfatin-1 receptor.

Further, GPR3 and GPR6 are known to form a family with GPR12. When the mutual homologies of an amino acid sequence of human GPR12 with an amino acid sequences of GPR6 and GPR3 were investigated (under the conditions of: Program: water, Matrix: EBLOSUM62, Gap_penalty: 10.0, and xtend_penalty: 0.5), it is shown that there is a high degree of homology where the identity of the amino acid residues is 57 to 59% and the similarity allowing substitution of the amino acid residues based on the properties is 73 to 76%, indicating that GPR12, GPR6 and GPR3 have structurally high similarities. Further, these receptors have properties common to GPR12 on the account of making use of S1P as a ligand. Therefore, it is expected by those skilled in the art that GPR3 and GPR6 function as "a Nesfatin-1 receptor" similarly to GPR12. The amino acid sequences of GPR3 and GPR6 are represented by SEQ ID NOs: 48 and 49, respectively.

In addition, instead of GPR3, GPR6 or GPR12, a modified form of GPR3, a modified form of GPR6 and a modified form of GPR12 that have amino acid sequences having 70% or more of homology with the amino acid sequence (GPR12) represented by SEQ ID NO: 7 or 8, the amino acid sequence (GPR3) represented by SEQ ID NO: 48 and the amino acid sequence (GPR6) represented by SEQ ID NO: 49, and that are able to be involved in a Nesfatin-1 action as described later, may be used and included within the scope of the present invention. In such case, the homology with the amino acid sequence represented by SEQ ID NO: 7, 8, 48 or 49 is preferably 80% or more and more preferably 90% or more. Further, a protein that has an amino acid sequence in which part of the amino acids is deleted, inserted or substituted in the amino acid sequence represented by SEQ ID NO: 7 or 8, and that may be involved in the Nesfatin-1 action may also be used. Such protein is, for example, in the amino acid sequence of SEQ ID NO: 7 or 8, obtained by substituting one or more of amino acid residues with the amino acids that have chemical properties or structures similar to those of the amino acid.

The specific embodiment of a substitution for such an amino acid that has chemical properties or structures similar to those of the amino acid, that is, a substitution for an amino acid that has high conservative properties, is widely known by those skilled in the art. For example, the chemical properties or structure of glycine (Gly) is similar to those of proline (Pro), alanine (Ala) and valine (Val); leucine (Leu) is to isoleucine (Ile), glutamic acid (Glu) is to glutamine (Gln); aspartic acid (Asp) is to asparagine (Asn); cysteine (Cys) is to threonine (Thr); Thr is to serine (Ser) and Ala; and lysine (Lys) is to arginine (Arg). In addition, as an alternative method, referring to an amino acid matrix expressing the ease of substitution of amino acid as a matrix, for example, PAM (Wilbur, Molecular biology and evolution, USA, Vol. 2, p434-447, 1985), and BLOSUM (Henikoff, Proceedings of the National Academy of Sciences of the United States of America, USA, Vol. 89, p10915-10919, 1992) and the like, substitution of an amino acid while considering height of its score is easily conducted by those skilled in the art. A protein having an amino acid sequence in which such amino acid is deleted, inserted or substituted, for example, may be identified as a protein involved in a Nesfatin-1 action, by producing genes in which mutation is introduced by appropriately conducting deletion, insertion or substitution on the base sequence of a gene encoding the Nesfatin-1 receptor (mGPR12) represented by SEQ ID NO: 7; then using the genes to prepare the Nesfatin-1 receptor-introduced cells as described later; and then detecting a binding to Nesfatin-1 or a cellular signal. Further, as a Nesfatin-1 receptor of the present invention, a protein involved in a Nesfatin-1 action, in which at least one amino acid residue in the amino acid sequence represented by SEQ ID NO: 7, 8, 48 or 49 is modified with a compound or a peptide, may be used.

Further, hereinafter, a receptor protein selected from the group consisting of GPR3, GPR6 and GPR12 is collectively referred to as "a Nesfatin-1 receptor" as a matter of convenience.

In the present invention, "Nesfatin-1 action" is a series of action caused by Nesfatin-1 and includes, for example, binding of Nesfatin-1 and a Nesfatin-1 receptor, signal transduction caused by the binding of Nesfatin-1 to a Nesfatin-1 receptor, response to outside cells caused by the signal transduction, furthermore, action for suppressing food intake and/or body weight gain, and the like. "Nesfatin-1-action regulating substance" is a substance regulating such Nesfatin-1-action, and a substance inhibiting or facilitating Nesfatin-1-action.

As a substance inhibiting Nesfatin-1-action, for example, an antagonist, an inverse agonist and a neutral antagonist for a Nesfatin-1 receptor are mentioned. In addition, there are also mentioned a substance that decreases the intensity or frequency of the signal transduction induced at the time of binding of Nesfatin-1 and a Nesfatin-1 receptor, a substance having the action of promoting the initiation, prolonging or sustaining of the unresponsive period during which the signals to be induced after a Nesfatin-1 receptor acts on Nesfatin-1 or other agonists are not generated (promoting/sustaining action of receptor internalization, inhibition of re-recruitment and the like), and others.

Further, as a substance facilitating Nesfatin-1-action, for example, an agonist for a Nesfatin-1 receptor, a substance that increases duration, or intensity or frequency of the signal transduction induced at the time of binding of Nesfatin-1 and a Nesfatin-1 receptor, and the like are mentioned. Further, herein, a substance having an agonistic activity on a Nesfatin-1 receptor is also referred to as "Nesfatin-1-like action substance".

In a method for screening a Nesfatin-1-action regulating substance of the present invention, a Nesfatin-1-action regulating substance is identified based on a change of Nesfatin-1 action. Such "a change of Nesfatin-1 action" includes the binding capacity of Nesfatin-1 with a Nesfatin-1 receptor, the signal transduction ability of a Nesfatin-1 receptor, a change of food intake behavior and/or action on body weight regulation, and the like.

Specifically, a Nesfatin-1-action inhibiting substance is identified as "a change of Nesfatin-1 action" based on the attenuation of Nesfatin-1 action. "The attenuation of Nesfatin-1 action" includes, for example, a decrease of binding of Nesfatin-1 to a Nesfatin-1 receptor caused by antagonism and the like with Nesfatin-1; and events such as an attenuation of G-protein-coupled signal, facilitation of food intake and/or increasing action of body weight and the like, which is caused by inactivation of a Nesfatin-1 receptor or antagonism with Nesfatin-1 and the like. By measuring these phenomena directly or indirectly, a Nesfatin-1-action inhibiting substance is identified.

On the other hand, a Nesfatin-1-action facilitating substance is identified as "a change of Nesfatin-1-action" based on the facilitation of Nesfatin-1 action. The facilitation of Nesfatin-1 action includes, for example, facilitation of binding of Nesfatin-1 to a Nesfatin-1 receptor, and events such as activation of the G-protein-coupled signal, food intake suppression and/or inhibitory action on body weight gain, and the like caused by activation of a Nesfatin-1 receptor and the like. By measuring these phenomena directly or indirectly, a Nesfatin-1-action facilitating substance is identified.

Measurement of the decrease or facilitation of binding of Nesfatin-1 to a Nesfatin-1 receptor is conducted by an analysis method generally used in the art, for example, a binding capacity assay such a FACS or BIAcore analysis, a FRET analysis, a direct binding assay classically used and the like. More specifically, evaluation of the binding of Nesfatin-1 to a Nesfatin-1 receptor is conducted by, for example, a system to quantify the binding of Nesfatin-1 labeled with $^{125}$I to Nesfatin-1 receptor-expressing cells. As cells used for this evaluation, Nesfatin-1 receptor-expressing cells as described later are used, and further, the evaluation may be conducted by using receptor-expressing cell membranes recovered after the cells are destroyed by homogenization. As a labeled Nesfatin-1, a Nesfatin-1 labeled with $^3$H in addition to that labeled with $^{125}$I is also used. The Nesfatin-1 labeled with $^3$H is obtained by expressing it in a cell system or a cell-free system according to the above-described method using an amino acid labeled with $^3$H, or by a peptide synthesis method. The binding level of radioisotope-labeled Nesfatin-1 to a Nesfatin-1 receptor is measured by using, for example, a gamma counter or a scintillation counter.

Further, the binding level of the labeled Nesfatin-1 to a Nesfatin-1 receptor may also be measured by labeling Nesfatin-1 with a fluorescent substance or a luminescent substance. Labeling with a fluorescent substance or a luminescent substance of Nesfatin-1 may be conducted by a method described in BIOCONJUGATE Techniques (Hermanson, Academic Press, 1996) and the like. The binding level of the Nesfatin-1 labeled with a fluorescent substance is measured by, for example, a fluorescence spectrophotometer, a flow cytometric method or the like. Further, the binding level of the Nesfatin-1 labeled with a luminescent substance is measured by, for example, a luminescence spectrophotometer, a scintillation counter method or the like. Furthermore, another labeling method of Nesfatin-1 is to bind an enzyme such as alkaline phosphatase, peroxidase and the like, and the binding level of Nesfatin-1 is determined by reacting a substrate for measuring their enzyme activity and measuring the coloring, fluorescence, luminescence and the like according to the properties of each substrate. The binding of an enzyme to Nesfatin-1 is conducted by using a method described in BIO-CONJUGATE Techniques (Hermanson, Academic Press, 1996) and the like. Further, the binding may be also conducted with genetic engineering by expressing a fusion protein using a DNA molecule encoding Nesfatin-1 and a DNA molecule encoding an enzyme such as alkaline phosphatase and the like (Hieshima et al., Journal of Immunology, Vol. 159, p1140-1149, USA, 1997). Further, the binding level may be measured by labeling Nesfatin-1 with biotin or a related substance thereof, and reacting the avidin or related protein thereof in which an enzyme, a fluorescent substance, a luminescent substance or the like is bound. Furthermore, a binding to a Nesfatin-1 receptor may be detected using unlabeled Nesfatin-1. One of the methods is a measurement by using surface plasmon resonance such as BIAcore(R) and the like, in which the binding of Nesfatin-1 to Nesfatin-1 receptor-expressing cells immobilized on a sensor or a cell membrane of the cells is measured by using a BIAcore(R) system (Biacore AB Corporation) and the like (Nagata and Handa (eds.), Real-Time Analysis of Biomolecular Interactions, Springer-Verlag, Tokyo, 1998). Further, the binding of Nesfatin-1 may be detected using BRET as an alternative method. In this method, firstly, a DNA encoding Nesfatin-1 receptor and a DNA encoding luciferase are used to construct a gene in such a manner that these DNAs are expressed as a fusion protein, and the gene is introduced into a cell. Another gene is constructed in such a manner that a fusion protein is expressed, where a fluorescent protein of *Aequorea victoria* is fused with an arrestin in which binding is formed when a receptor is activated, and the gene is introduced into the cell at the same time. Then, by reacting the latter with the luminescent substrate of luciferase, the photo-energy from the luminescent substrate is transferred to the fluorescent protein of *Aequorea victoria* only when Nesfatin-1 binds to the receptor, resulting in a wavelength shift. Finally, the binding level of Nesfatin-1 is determined by measuring the wavelength shift (Packard BioScience Co., Application Note #BLT-001).

The measurement of an attenuation or activation of G-protein-coupled signal transduction ability by a Nesfatin-1 receptor is conducted using a direct or indirect method. (Morris et al., Physiological Reviews, 1999, Vol. 79, p1373-1430). In a direct method, the measurement is conducted by the detection of the state of GDP-GTP exchange in a G-protein coupled with a receptor, the increase or decrease in the intracellular cAMP level, the generation of inositol triphosphate by the action of phospholipase C, the increase or decrease in intracellular calcium ion level, the internalization of a Nesfatin-1 receptor and the like, as an indicator. In an indirect method, the measurement may be conducted via an indicator such as proliferation of cells, morphological change, migration, luminescence and the like. In the evaluation by this measurement, depending on the purpose, Nesfatin-1 receptor-expressing cells as described later or cell membranes in which a receptor is expressed are removed after destroying the cells using homogenization, may also be used. Further, those skilled in the art may appropriately make up the measurement methods by combining the cells or cell membrane with necessary reagents and/or devices.

As a method for directly measuring cellular signals, more specifically, as a method for measuring GDP/GTP exchange reaction in a coupled G protein, a method of measuring the level of GTP analogs such as radiolabeled GTP-$\gamma$S and the like incorporated into a coupled G protein (Gs) when Nesfatin-1 or a modified peptide as described later or other test substances are reacted with Nesfatin-1 receptor-expressing cells or cell membranes in which a receptor is expressed recovered after destroying the cells using homogenization may be used. In this case, as a radiolabeling, $^{35}$S, $^{32}$S, $^{3}$H and the like may be used appropriately.

Further, as an alternative method for directly measuring cellular signals, a measurement of the decrease or increase of cAMP production is mentioned, and there is used a method of reacting Nesfatin-1 or a modified peptide as described later or other test substances with Nesfatin-1 receptor-expressing cells and measuring the level of intracellular cAMP. Here, since GPR12 that is a Nesfatin-1 receptor is coupled with a Gs type G protein, the action is detected as an increase of intracellular cAMP in the activated state of the receptor. The measurement of the level of cAMP is conducted by using a commercially available ELISA kit (Cayman, Cat#581101 and the like), a cAMP AlphaScreen camp assay kit (Cat. No. 6760600) manufactured by PerkinElmer, Inc., and the like, but not limited to them.

As described above, when the intracellular cAMP level is increased, the intracellular signaling system consecutively reacts to activate the gene expression in cells. A typical example of such activation is represented by a pathway, where a protein kinase A (PKA) that is activated cAMP-dependently activates by phosphorylating the CREB (CRE-binding protein) that is a transcription factor binding to CRE (cAMP responsive element) on a genomic gene, and the activated CREB subsequently induces a transcription of a gene located downstream of the CRE (Ralli et al., The Journal of Biological Chemistry, Vol. 269, p17359-17362, 1994). Therefore, a component in this pathway may be used for a method of measuring cellular signals, and for example, signals may be measured by activation of PKA, phosphorylation of CREB, expression of the gene located downstream of CRE, and the like. As an actual example, a measurement method by the phosphorylation of CREB is illustrated in Example 7, and a measurement method by the change of enzyme activity according to the expression of the reporter gene (an indicator gene for the expression of a target gene) located downstream of CRE is illustrated in Example 8, but it is not limited to them, and the measurement system may be appropriately constructed by those skilled in the art.

Further, there is mentioned another method for directly measuring cellular signals, in which the generation of inositol triphosphate by the action of phospholipase C and G protein signals caused by the increase or decrease in intracellular calcium ion level are detected. Uhlenbrock et al. have reported that the increase in cytoplasmic calcium ion concentration occurs when S1P and SPC are acted in cells in which a GPR12 gene is introduced and expressed (Cell Signal. 2002 Nov., 14(11):941-53). Further, the generation of inositol triphosphate by the action of phospholipase C and the increase or decrease in the intracellular calcium ion level are well known as a reaction of G protein classified to Gq type or G11 type. However, when G$\alpha$15 or G$\alpha$16 has been expressed in cells, even in the reaction of GPCR coupled with Gs type G protein, the generation of inositol triphosphate and the influx reaction of intracellular calcium to the cytoplasm may be recognized. Therefore, the generation of inositol triphosphate and the increase or decrease in intracellular calcium ion level are conducted by reacting Nesfatin-1 or a modified peptide as described later or other test substances with Nesfatin-1 receptor-expressing cells in which G$\alpha$15 or G$\alpha$16 is expressed, and then measuring the inositol triphosphate level and the variation of the intracellular calcium ion. Here, the measurement of intracellular IP3 is performed by a known method. For example, a combination of Alpha Screen IP3 assay supplement (Cat. No. 6760621) and a GST detection kit (Cat. No. 6760603) manufactured by PerkinElmer, Inc., and the like is used. Further, influx reaction of calcium ions to the cytoplasm is frequently conducted by a method of observing the change in an intracellular calcium concentration based on the wavelength shift of fluorescence using a Fura2-AM reagent, and a reagent such as Fura3 and the like may be used instead of Fura2-AM. Furthermore, as a method for measuring the influx of calcium ions to the cytoplasm, detection by emission may be used by injecting or expressing calcium-binding photoprotein aequorin to the Nesfatin-1 receptor-expressing cells (Le Poul et al., Journal of biomolecular screening: the official journal of the Society for Biomolecular Screening, Vol. 7, p57-65, 2002).

In addition, an example of the method for directly measuring cellular signals includes a method of detecting the unresponsive state of a ligand after Nesfatin-1 is reacted with the Nesfatin-1 receptor-expressing cells. It is known that a G-protein-coupled receptor is reacted with a ligand, and then incorporated to cells by internalization, and that as a result of the internalization, the receptor disappears from the cell surface or has a certain period of time incapable of being reacted with a ligand. Therefore, for example, for the analysis of the receptor internalization, there is mentioned a method of investigating the distribution of a Nesfatin-1 receptor in a cell membrane and cells using a confocal laser scanning microscope, by binding a fluorescent protein such as GFP and the like to N-terminus or C-terminus of the Nesfatin-1 receptor or by reacting with a fluorescence-labeled antibody recognizing a Nesfatin-1 receptor, when Nesfatin-1-introduced cells as described later are prepared. Further, as for the measurement of the unresponsive period of cells and the intensity of signals, for example, a measurement method is appropriately constructed by measuring the reaction intensity when a ligand such as Nesfatin-1 and the like is reacted once with Nesfatin-1 receptor-expressing cells in which $G\alpha 15$ or $G\alpha 16$ is expressed in the presence of a test substance while monitoring calcium ions in the cytoplasm and further reacted with the cells once or more, or by measuring the time until the reactivity is obtained again, or the like.

The process of making a test substance act on a coexisting system of Nesfatin-1 and a Nesfatin-1 receptor is conducted by making the test substance act on Nesfatin-1 receptor-expressing cells or a Nesfatin-1 receptor-expressing non-human animal together with Nesfatin-1.

Nesfatin-1 receptor-expressing cells include, for example, "Nesfatin-1 receptor-introduced cells" prepared by genetic recombination, or the cells or cell lines obtained from an animal expressing a Nesfatin-1 receptor, or the like.

"Nesfatin-1 receptor-introduced cells" are obtained with transformation by introducing a gene encoding a Nesfatin-1 receptor into a host cell in order to transiently or stably express a Nesfatin-1 receptor. As a transformation method, for example, a general method in the art such as a biological method, a physical method, a chemical method and the like is used. As a biological method, for example, a method of using a viral vector, a method of using a specific receptor, a cell fusion method (hemagglutinating virus of Japan (HVJ)), a method of using polyethylene glycol (PEG), an electric cell fusion method, and a micronuclear fusion method (chromosome transfer) are mentioned. As a physical method, a microinjection method, an electroporation method, and gene gun technology are mentioned. As a chemical method, a calcium phosphate precipitation method, a liposome method, a DEAE-dextran method, a protoplast method, an erythrocyte ghost method, an erythrocyte membrane ghost method, and a microcapsule method are mentioned. From them, an appropriate method may be selected and used by those skilled in the art (Yokota and Arai (eds.), Biomanual Series 4, Gene Transfer and Expression Analysis, Yodosha, 1994, and Harbin; Cloning, Gene Expression and Protein Purification: Experimental Procedures and Process Rationale; Oxford University Press; 2001).

A host cell used for transformation includes HeLa cells, HEK293 cells, COS7 cells, CHO cells, dividing yeast cells, budding yeast cells and the like.

Further, as Nesfatin-1 receptor-expressing cells, cells obtained from an animal organ may be used. As such an organ, an organ of mammals, preferably a brain (hypothalamus, hippocampus), a liver, adipose tissues, muscle tissues and the like are mentioned. In addition, cells isolated from an organ of a Nesfatin-1 receptor-expressing non-human animal as described later and the like are also mentioned.

Furthermore, as Nesfatin-1 receptor-expressing cells, a cultured cell line may be used. As such a cultured cell line, a HT22 cell line that is a mouse hippocampus-derived cell line, a human umbilical vein endothelial cell (HUVEC), Hep3B cells (ATCC No. HB-8064) that is a human hepatoma cell line, and the like are mentioned (Cell Physiol Biochem 13: p75-p84, 2003; J Neuroscience 23(3), p907-p914, 2003).

"A Nesfatin-1 receptor-expressing non-human animal" herein refers to a non-human animal expressing a Nesfatin-1 receptor at a higher level than the average level in a genetically same kind of animal; a non-human animal in which Nesfatin-1 receptor-introduced cells, in which a Nesfatin-1 receptor is expressed transiently or stably, is transplanted by introducing a Nesfatin-1 receptor; or a Nesfatin-1 receptor-introduced non-human animal.

"A Nesfatin-1 receptor-introduced non-human animal" specifically refers to a transgenic non-human animal expressing a Nesfatin-1 receptor transiently or stably by introducing a gene encoding a Nesfatin-1 receptor so that a Nesfatin-1 receptor may be overexpressed. The "Nesfatin-1 receptor-expressing non-human animal" may be prepared by using a method for obtaining an ordinary transgenic animal. For example, the transgenic animal is obtained by using a method in which a gene and an egg are mixed and treated with calcium phosphate, a method of directly introducing a gene to a nucleus in a pronuclear-stage egg by a micropipette under a phase-contrast microscope (microinjection method, U.S. Pat. No. 4,873,191), a method of using embryonic stem cells (ES cells), and the like. In addition, a method of infecting an egg with a retroviral vector into which a gene is inserted, a sperm vector method of introducing a gene into an egg via a sperm, and the like have been developed. The sperm vector method is a genetic recombination method in which a foreign gene is incorporated into a sperm cell, by either attaching the gene to a sperm or using a method such as an electoporation method and the like, and then fertilizing an egg by the sperm (Lavitranoet M et al., Cell (1989) 57, 717-723).

Further, in a screening method using "a Nesfatin-1 receptor-expressing non-human animal", "a change of Nesfatin-1 action" may be detected by screening "a Nesfatin-1-action regulating substance" based on a change of an action for suppressing food intake and/or body weight gain.

As "a test substance" in a method of the present invention, a peptide or a peptide analog obtained by modifying a peptide having the amino acid sequence represented by any of SEQ ID NOs: 1 to 3 or 11 to 37 is used. By using such a peptide or peptide analog, accuracy of the screening can be improved.

As such a modified peptide, a peptide composed of an amino acid sequence having at least 60% or more of homology with the amino acid sequence represented by any of SEQ ID NOs: 1 to 3 or 11 to 37 is mentioned. The homology with the amino acid sequence represented by any of SEQ ID NOs: 1 to 3 or 11 to 37 is preferably 70% or more, and more preferably 80% or more. As a peptide analog, in the amino acid sequence represented by any of SEQ ID NOs: 1 to 3 or 11 to 37, a peptide composed of an amino acid sequence in which part of the amino acids is deleted, inserted or substituted is mentioned. Such a peptide is, for example, obtained by substituting one or more amino acid residues with the amino acids that have chemical properties or structures similar to those of the amino acid in the amino acid sequence represented by any of SEQ ID NOs: 1 to 3 or 11 to 37. The specific embodiment of a substitution for such amino acid that has chemical properties or structures similar to those of the amino acid, that is, a substitution for an amino acid that has high conservative properties, is widely known by those skilled in the art. For example, glycine (Gly) is similar to proline (Pro), alanine (Ala) and valine (Val); leucine (Leu) is to isoleucine (Ile), glutamic acid (Glu) is to glutamine (Gln); aspartic acid (Asp) is to asparagine (Asn); cysteine (Cys) is to threonine (Thr); Thr is to serine (Ser) and Ala; and lysine (Lys) is to arginine (Arg), in terms of the chemical properties or structure. In addition, as for another method, referring to an amino acid matrix expressing the ease of substitution of amino acid as a matrix, for example, PAM (Wilbur, Molecular biology and evolution, USA, Vol. 2, p434-447, 1985), and BLOSUM (Henikoff, Proceedings of the National Academy of Sciences of the United States of America, USA, Vol. 89, p10915-10919, 1992) and the like, substitution of an amino acid while considering height of its score is easily conducted by those skilled in the art.

A peptide analog also includes peptide analogs in which at least one of the amino residues of the amino acid sequence represented by any of SEQ ID NOs: 1 to 3 or 11 to 37 is modified with a compound or a peptide. In this case, an example of the compound includes a substance such as sugar, lipid, a nucleic acid, an amine and the like, and an artificially-synthesized compound. In addition, a peptide in this case refers to an oligopeptide or protein in which one or more amino acids are bonded, and includes an oligopeptide or protein in which the compound per se or peptide per se has or does not have a function independently from the amino acid sequence represented by any of SEQ ID NOs: 1 to 3 or 11 to 37. Further, the peptide analog also includes a compound designed and synthesized based on the structural information of Nesfatin-1 or a Nesfatin-1 receptor, for example, a peptide mimic, a peptoid and the like.

Furthermore, "a test substance" provided in a screening method of the present invention is not particularly limited, and other peptides, antibodies, compounds and the like may be used.

In addition, the present invention relates to a Nesfatin-1-action regulating substance obtained by the above-mentioned screening method. Such a Nesfatin-1-action regulating substance includes a Nesfatin-1-action inhibiting substance and a Nesfatin-1-action facilitating substance. A Nesfatin-1-action inhibiting substance is, for example, an antagonist, an inverse agonist and a neutral antagonist for a Nesfatin-1, and is used for prevention or treatment of a disease involved in a nutritional/eating disorder such as a decreased appetite, an anorexia and the like in a postoperative patient and/or a patient suffering from cancer.

A Nesfatin-1-action facilitating substance is, for example, an agonist for a Nesfatin-1, and is used for prevention or treatment of a disease associated with adipositas such as a disease involved in metabolism/eating disorder such as obesity or adiposis, bulimia nervosa and the like; type 2 diabetes mellitus; impaired glucose tolerance; hypertension; hyperlipidemia; hyperuricemia; fatty liver; heart disease; cerebrovascular disease; sleep apnea syndrome; an orthopedic disease such as osteoarthritis and the like; menstrual abnormality; malignant tumor and the like.

<A Method for Screening a Nesfatin-1-Like Action Substance>

The present invention also relates to a method for screening a Nesfatin-1-like action substance comprising steps of making a test substance act on a Nesfatin-1 receptor and of identifying the Nesfatin-1-like action substance based on a change of Nesfatin-1 action.

In the present invention, "a Nesfatin-1-like action substance" denotes a substance having an action similar to the "Nesfatin-1 action" as described above, and includes a substance having a stronger Nesfatin-1 action, a super agonist and the like.

In the present invention, "a Nesfatin-1 action" is as described in <A method for screening a Nesfatin-1-like action substance>, and "a Nesfatin-1-like action substance" may be screened based on, for example, "the binding capacity of a Nesfatin-1 receptor" or "the signal transduction ability of a Nesfatin-1 receptor."

"The binding capacity of a Nesfatin-1 receptor" is evaluated by detecting a facilitation event of the binding of a test substance to a Nesfatin-1 receptor.

The measurement of the facilitation of the binding of Nesfatin-1 to a Nesfatin-1 receptor is conducted, as described above, by an analysis method generally used in the art, for example, an analysis of binding capacity such as FACS or BIACORE, FRET, a classical direct binding assay, and the like.

"The signal transduction ability of a Nesfatin-1 receptor" may be measured by conducting a direct or indirect method. In a direct method, the measurement may be conducted by detecting of the state of GDP-GTP exchange in a G-protein coupled with a receptor, the increase or decrease in the intracellular cAMP level, the generation of inositol triphosphate by the action of phospholipase C, the increase or decrease in the intracellular calcium ion level, the internalization of a Nesfatin-1 receptor and the like, as an indicator. In an indirect method, the measurement may be conducted via an indicator such as proliferation of cells, morphological change, migration, luminescence and the like. "The binding capacity of a Nesfatin-1 receptor" or "the signal transduction ability of a Nesfatin-1 receptor" is measured by using a method as described in <A method for screening a Nesfatin-1-like action substance>.

The step of making a test substance act on a Nesfatin-1 receptor may be conducted by making a test substance act on Nesfatin-1 receptor-expressing cells or a Nesfatin-1 receptor-expressing non-human animal. "Nesfatin-1 receptor-expressing cells" and "a Nesfatin-1 receptor-expressing non-human animal" are as described before in <A method for screening a Nesfatin-1-like action substance>.

As "a test substance" in a method of the present invention, for example, a peptide or a peptide analog obtained by modifying a peptide having the amino acid sequence represented by any of SEQ ID NOs: 1 to 3 or 11 to 37 may be used, but it is not limited to them. By using such a peptide or peptide analog, accuracy of the screening can be improved.

Further, such "a modified peptide" and "a modified peptide analog" are as described in <A method for screening a Nesfatin-1-like action substance>. "A test substance" as used for a screening method of the present invention is not particularly limited. Other peptides, antibodies, compounds and the like may be used.

Further, the present invention also relates to a Nesfatin-1-like action regulating substance obtained in the above-mentioned screening method. Such a Nesfatin-1-like action substance is, for example, a superagonist for Nesfatin-1, and is used for prevention or treatment of a disease associated with adiposis such as a disease involved in metabolism/eating disorder such as obesity or adiposis, bulimia nervosa and the like; type 2 diabetes mellitus; impaired glucose tolerance; hypertension; hyperlipidemia; hyperuricemia; fatty liver; heart disease; cerebrovascular disease; sleep apnea syndrome; orthopedic disease such as osteoarthritis and the like; menstrual abnormality; malignant tumor and the like.

<A Method for Screening a Nesfatin-1-Action Regulating or Nesfatin-1-Like Action Substance in Silico>

The present invention further relates to a method for screening in silico or designing a Nesfatin-1-action regulating substance or a Nesfatin-1-like action substance; based on a Nesfatin-1 receptor structure or a ligand structure, wherein the Nesfatin-1 receptor structure is obtained by a simulation based on a known structure information of GPR3, GPR6 or GPR12.

In the present invention, "known structure information of GPR3, GPR6 or GPR12" denotes information of a three-dimensional structure of GPR3, GPR6 or GPR12 obtained by a method such as homology modeling and the like using a structure of GPR3, GPR6 or GPR12 that has been already elucidated, for example, three-dimensional structure data from bovine rhodopsin. Such modeling is conducted with reference to a method described by, for example, Ballesteros J, Curr Opin Drug Discov Devel, 2001, 4(5) p561-574; Trabamino R J, Biophysical Journal, Volume 86, April 2004, p1904-1921; Vaidehi N, THE JOURNAL OF BIOLOGICAL CHEMISTRY, Vol. 281, 2006, p27613-27620; and the like. Further, a method for screening in silico or for designing using structure information of GPR3, GPR6 or GPR12 may be appropriately conducted by those skilled in the art with reference to a method described by, for example, Ballesteros J, Curr Opin Drug Discov Devel, 2001, 4(5) p561-574; Reggio P H et al., The AAPS Journal, 2006, 8 (2) Article 37, pE322-E326; Becker O M, Proceedings of the National Academy of Sciences of the United States of America, Vol. 101, 2004, p11304-11309; Kortagere S. et al., Journal of Computer-aided molecular design, Vol. 20, 2006, p789-802; and the like.

Further, a method for designing a synthetic compound acting on GPR3, GPR6 or GPR12 from a structure of the Nesfatin-1 that is a ligand, may be conducted with reference to a method described by, for example, Goede A et al., BMC Bioinfomatics, Vol. 7, 2006, p1-5; James et al., Bioorganic & medicinal chemistry letters, Vol. 16, p5462-5467; and the like.

EXAMPLES

Example 1

<Preparation of Recombinant Nesfatin-1>

A gene encoding a mouse Nesfatin-1 was obtained, and a gene of GST (glutathione S-transferase) and a histidine tag were bonded at the N-terminus of the gene encoding a mouse Nesfatin-1, and then an expression vector was constructed so that a cleavage site (-Leu-Val-Pro-Arg-Gly-Ser-) by thrombin may intervene between an amino acid sequence of a histidine tag and an amino acid sequence of the mouse Nesfatin-1 in a protein after translation. A gene of the mouse Nesfatin-1 was obtained by performing PCR (Nested PCR) twice using a mouse Brain cDNA (Clontech Laboratories). The reaction of PCR in the first round was performed by using the following Forward (mNucB2-F337, SEQ ID NO: 38) and Reverse (mNucB2-R712, SEQ ID NO: 39) at each concentration of 100 pM, Pyrobest DNA polymerase (TAKARA BIO INC., R005A), the attached reaction buffer and dNTP, in accordance with the attached protocol. The PCR reaction was performed 30 cycles of the temperature cycle at 98° C. for 10 seconds and 68° C. for 1 minute after the reaction at 90° C. for 1 minute, and then under the temperature condition of 68° C. for 2 minutes.

```
Forward Primer (mNucB2-F337):
                                  (SEQ ID NO: 38)
5'-GCACGCTGAC CGCTC TGGAAG-3'

Reverse Primer (mNucB2-R712):
                                  (SEQ ID NO: 39)
5'-CAAATGTGTT AGGAT TCTGGTGGTTCA-3'
```

Using 0.5 µL of the obtained PCR product, the reaction of PCR in the second round was performed with 100 pM primer of the following Forward (mNucB2-N3-[SacI-Thr]) and Reverse (mNucB2-R389-[NotI]), similarly to the PCR reaction in the first round, by using Pyrobest DNA polymerase. The PCR reaction was performed 20 cycles of the temperature cycle at 98° C. for 10 seconds, 60° C. for 30 seconds, and 68° C. for 1 minute after the reaction at 90° C. for 1 minute, and then under the temperature condition of 68° C. for 2 minutes.

```
Forward Primer (mNucB2-N3 [SacII-Thr]):
                                  (SEQ ID NO: 40)
5'-GGTTCCGCGGGTCTGGTTCCGCGTGGTTCTCCTATCGATGTG
GACAAGACCAA-3'

Reverse Primer (mNucB2-R589[NotI]):
                                  (SEQ ID NO: 41)
5'-GGTTGCGGCCGCTTACCTCT TCAGCTCATCCAGTCTCG-3'
```

PCR reaction sample obtained after performing the second-round PCR was purified by phenol/chloroform extraction, and then cleaved by restriction enzymes SacII and NotI. The fragments were subjected to agarose gel electrophoresis, from which a band corresponding to the length of ca. 300 bp was cut out, and purified using a QIAEX-II kit (QIAGEN Inc.). The purified PCR product with ca. 300 bp was subjected to ligation using a Quick DNA ligase kit (New England Biolabs, Inc.) to a pET41a (+) plasmid vector (Novagen) cleaved by restriction enzymes SacII and NotI. A ligated vector was introduced into an *Escherichia coli* strain JM109, a small-scale plasmid extraction was performed with the obtained 8 transformants, and DNA sequence analysis of the inserted Nesfatin-1-gene sequence of the obtained plasmid was performed by using a BigDye Terminator Cycle Sequencing FS Ready Reaction kit (Applied Biosystems Co., Ltd.) and ABI377 DNA Sequencer (Perkin-Elmer Co., Ltd.). As a result, an expression vector in which a gene having a correct mouse Nesfatin-1 DNA sequence was inserted was obtained and named "pET41a(+)GST-His-LVPRGS-mNAP1".

The obtained pET41a(+)GST-His-LVPRGS-mNAP1 was introduced into an *Escherichia coli* BL21 (DE3) Codon Plus RIPL and expressed, and as a result, a fusion protein (GST-His-LVPRGS-mNAP1) of GST/histidine tag/thrombin cleavage sequence/Nesfatin-1 was expressed. pET41a(+)GST-His-LVPRGS-mNAP1 was introduced into an *Escherichia coli* BL21(DE3) Codon Plus RIPL, and then a clone was obtained by the selection in Luria-Bertani (LB) plate containing kanamycin and cultured in LB broth containing kanamycin at 37° C. The cultivation was terminated at a time when the absorbance at 600 nm reached 0.8 in the culture solution. A 3-mL aliquot of the culture was subcultured to the 100 mL of LB broth containing kanamycin, and the resultant broth was further cultured at 37° C., and at a time when the absorbance at 600 nm reached 0.8 in the culture, 1 mL of 100 mM IPTG (isopropyl thiogalactoside) was added to induce protein expression. After adding IPTG, the resultant broth was further cultured at 37° C. for 3 hours while shaking. The resultant culture was centrifuged at 8000 rpm (at 4° C.) for 20 minutes to recover the biomass the *Escherichia coli*.

A fusion protein (GST-His-LVPRGS-mNAP1) was extracted from the obtained *Escherichia coli* biomass, and purified using a nickel-chelate column (Ni-NTA agarose). The biomass was suspended in 20 mL of Sonication Buffer (50 mM $KH_2PO_4$, 50 mM NaCl, 2 mM DTT, pH 7.5) containing one-fold concentration of Complete-EDTA free (Roche Diagnostics K.K.) and 0.5-fold concentration of Bug-Buster (Merck, Novagen Cat. No. 70584), and fractured by sonication in ice water for 10 minutes. Sample obtained by the sonication was centrifuged at 15,000 rpm for 20 minutes to recover the supernatant. A 10-mL aliquot of the obtained supernatant was applied to 1 mL of Ni-NTA agarose column equilibrated with Lysis Buffer (50 mM $NaH_2PO_4$, 300 nM NaCl, 10 mM imidazole, pH 8.0), and then washed twice with 10 mL of Wash Buffer (50 mM $NaH_2PO_4$, 300 mM NaCl, 20 mM imidazole, pH 8.0). The column after washing was eluted twice with 2.5 mL of Elution Buffer (50 mM $NaH_2PO_4$, 300 mM NaCl, 250 mM imidazole, pH 8.0), and a fraction containing the eluted fusion protein (GST-His-LVPRGS-mNAP1) was recovered. The extracted supernatant from the remaining biomass was treated similarly, and a fraction containing the fusion protein (GST-His-LVPRGS-mNAP1) was recovered.

A part of the GST and histidine tag was removed from the fusion protein (GST-His-LVPRGS-mNAP1) and the remaining portion was further purified, and furthermore, in order to remove *Escherichia coli*-derived lipopolysaccharide (LPS) acting as an inflammatory substance, purification was performed by thrombin treatment and reversed-phase chromatography for the fusion protein (GST-His-LVPRGS-mNAP1) in the bonded state to a GST resin. Further, in the subsequent treatment, the buffer that had been confirmed to be free from LPS was used. A 7.2-mL aliquot of the fraction containing the fusion protein (GST-His-LVPRGS-mNAP1) obtained by the purification in the Ni-NTA agarose column was washed with one-fold concentration of GST Bind/Wash Buffer (Merck, Novagen Cat. No. 70571), and finally the fraction was added to the GST resin (Merck, Novagen Cat. No. 70541) (equivalent to 7.2 ml) suspended in 3 mL of GST Bind/Wash Buffer, and the resultant mixture was gently stirred at 20° C. for 1 hour. The resin was recovered by centrifugation, and then washed twice with 36 mL of GST Bind/Wash Buffer. A 3.6-mL aliquot of a solution in which 20 μunits/mL of thrombin was dissolved, was added to and suspended in the washed resin, and the resultant was reacted for 20 hours while gently stirring at 20° C. The resin after completion of the reaction was aliquoted by 1.8 mL in cups (millipore) with a filter having a pore size of 0.22 μn, centrifuged at 3,000 rpm for 2 minutes, and then filtered samples after thrombin treatment were recovered. To 450 μL of the obtained sample after thrombin treatment, 50 μL of acetic acid was added to prepare a sample for C18 reversed-phase chromatography. The reversed-phase chromatography analysis was performed by using a gradient elution method of acetonitrile in the presence of 0.1% trifluoroacetic acid, and setting the gradient as follows: 10% acetonitrile for 10 minutes, 10 to 20% acetonitrile gradient in 60 minutes, 30 to 40% acetonitrile gradient in 40 minutes, and 40 to 60% acetonitrile gradient in 5 minutes. The protein eluted from the column was monitored by measuring the absorbance at 280 nm. When the fraction eluted by the gradient of acetonitrile was analyzed by an SDS-PAGE analysis and a Western blotting analysis, it was found that Nesfatin-1 was eluted at the acetonitrile concentration of 36.2%. Therefore, the fraction was recovered and freeze-dried, and then the resultant sample was redissolved in distilled water for injection, and the recombinant mouse Nesfatin-1 was obtained.

<Selection of Nesfatin-1 Receptor Candidates>

A receptor for a peptide involved in food intake regulation is roughly classified into Cytokine Receptor Type represented by a leptin receptor and GPCR represented by an α-MSH receptor (=MC4R, MC3R). Therefore, firstly, analysis of GPCR was initiated.

An analysis of the action of Nesfatin-1 was performed using GPCRs picked up respectively by the following three methods (Examples 2 and 3) as a candidate of a Nesfatin-1 receptor (described in Examples 5 and 6).

Example 2

<Pickup of GPCR Having Fluctuating Expression by Nesfatin-1 Administration>

An ICR mouse (Japan SLC, Inc.) was administered intraperitoneally with the recombinant mouse Nesfatin-1 (0.5 mg/head) or saline immediately before the dark phase, from which the hypothalamus was collected 2 hours later. RNA extraction from the collected tissues was performed using ISOGEN™ (NIPPON GENE CO., LTD.) in accordance with the attached protocol. An expression analysis was performed with a mouse DNA array (47000 genes) of Illumina, Inc. using the extracted RNA (outsourced to Illumina, Inc.). As a result, GPCRs for which the fluctuating expression was confirmed by the administration of the recombinant mouse Nesfatin-1 compared with the administration of saline, were picked up.

Example 3

<Pickup of GPCR Having High Expression in Hypothalamus>

A total RNA (BD Bioscience) of the whole brain and hypothalamus of a mouse was purchased, and an analysis was performed (outsourced to Hokkaido System Science Co., Ltd.) with a mouse DNA microarray "Whole Mouse Genome Oligo Array" of Agilent Technologies (Cat. No. G4122A (Version of 10 Oct., 2005) having around 40,000 genes, the gene list is available from the internet website of Agilent Technologies, RefSeq, RIKEN Build 7.1, USCS GoldenPath, Ensemble, NIA Mouse Gene Index, UniGene Build 135, MGI, NCBI Mouse genome Build 32). Orphan GPCRs in which expression intensity in hypothalamus is higher than that in the whole brain were picked up.

Example 4

<Construction of Candidate GPCR Expression Vector>

As for 33 kinds of GPCRs picked up in Examples 2 and 3, PCR cloning was performed based on a cDNA sequence of GenBank using a cDNA of hypothalamus as a template. Amplified DNA fragments were ligated into an expression vector of pEF1/MycHisA (Invitrogen Corporation) or pEF4/

MycHisA (Invitrogen Corporation) and the base sequence was determined, from which a candidate GPCR expression vector was constructed.

Example 5

<Evaluation of Camp Production in HeLa-Cell Transient Expression System>

A GPCR expression vector prepared in Example 4 was introduced into HeLa cells by lipofection and transiently expressed.

HeLa cells were peeled off using trypsin EDTA and recovered, and plated onto a 6-well plate with $7\times10^5$ cells/2 mL/well to perform overnight culture using a $CO_2$ incubator. The next day, a plasmid solution was prepared by adding 4 µg of plasmid into 250 µL of a serum-free Opti-MEM medium. On the other hand, a Lipofectamine 2000 solution was prepared by adding 10 µL of Lipofectamine 2000 (Invitrogen Corporation) into 250 µL of the serum-free Opti-MEM medium. These solutions were incubated at room temperature for 5 minutes, and the Lipofectamine 2000 solution was added bit by bit into the plasmid solution. The resultant mixture was incubated at room temperature for 20 minutes to prepare a solution for lipofection. After removing the supernatant, the HeLa cells were washed once with Opti-MEM and 2 mL of Opti-MEM was added to the cells, and then the above-mentioned solution for lipofection was added bit by bit to the HeLa-cell culture medium while shaking gently. The resultant mixture was cultured for 5 hours in a $CO_2$ incubator, and, after exchanging the medium with a serum-containing medium, the resultant culture solution was further cultured in a $CO_2$ incubator. The next day, transfection cells were peeled off using trypsin, suspended in the serum-containing medium and the cells were precipitated by centrifugation. The cells were then suspended in a serum-free medium and further centrifuged, and suspended again in the serum-free medium and further centrifuged, and finally a $1\times10^6$ cells/mL of cell suspension was prepared in the serum-free medium.

This suspension was plated onto a 96-well plate by 100 µL ($1\times10^5$ cells/well) per well and then cultured overnight in a $CO_2$ incubator.

Transiently expressing HeLa cells were washed once with the serum-free medium, and then the serum-free medium was added at 80 µL/well. A ligand solution with a 5-fold concentration (recombinant mouse Nesfatin-1 or α-MSH (used as a positive control)) was prepared with the serum-free medium.

The 5× Ligand solution was added at 20 µL/well so that the final concentration may become $10^{-6}$ M, and the plate was incubated in a $CO_2$ incubator for 30 minutes. When Forskolin that is an adenylate cyclase activator was added, it was added so that its final concentration may become 2 µM, and the plate was further incubated for 30 minutes. Subsequently, after removing the medium, a lysis buffer was added at 200 µL/well and the plate was shaken, and then the plate was incubated in a $CO_2$ incubator for 30 minutes to be lysed thoroughly. Further, in order to lyse the cells completely, the cells were frozen once at −20° C. and lysed again, and then the intracellular cAMP concentration was measured using cAMP-Screen System (Applied Biosystems, T1500).

Figure 2:
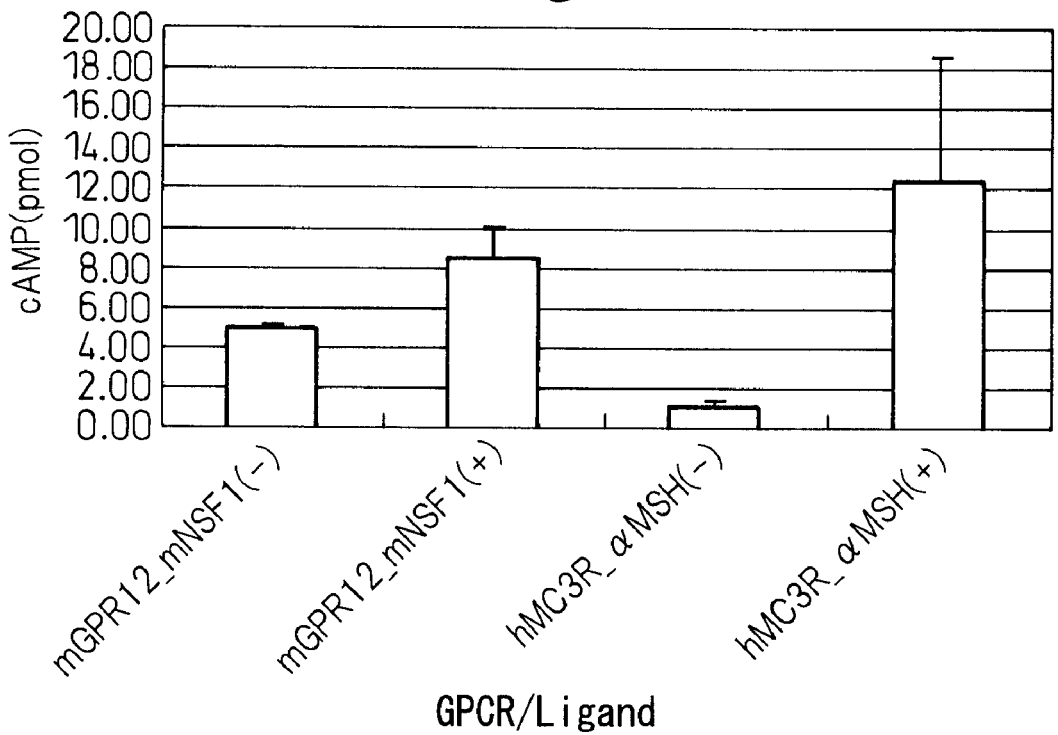
FIG. 2 is a bar graph showing the results comparing the cAMP production level in the presence of Forskolin for mGPR12-transiently expressing HeLa cells and hMC3R-transiently expressing HeLa cells. mGPR12_mNSF1(−) represents mGPR12-transiently expressing HeLa cells without mNSF1 addition, and mGPR12_mNSF1(+) represents mGPR12-expressing cells with mNSF1 addition. As a positive control, hMCR$_3$R_αMSH(−) represents hMC3R-transiently expressing HeLa cells without αMSH addition, and hMCR$_3$R_αMSH(+) represents hMC3R-transiently expressing HeLa cells with αMSH addition. The number of N is 3 (n=2 for hMC3R). SD is shown by a bar.

As a result of the measurement of the intracellular cAMP concentration, among 33 kinds of GPCRs expressing in the hypothalamus, the increase in the intracellular cAMP production was observed in mGPR12 by adding the recombinant mouse Nesfatin-1. Results of the measurements performed for mGPR12 are shown in FIGS. 1 (without Forskolin addition) and 2 (with Forskolin addition). In FIGS. 1 and 2, mGPR12_mNSF1(−) represents mGPR12-transiently expressing HeLa cells without recombinant mouse Nesfatin-1 addition, mGPR12_mNSF1(+) represents mGPR12-expressing cells with recombinant mouse Nesfatin-1 addition, hMCR₃R_αMSH(−) represents hMC3R-transiently expressing HeLa cells without αMSH addition, and hMCR₃R_αMSH(+) represents hMC3R-transiently expressing HeLa cells with αMSH addition. The hMC3R_α-MSH was used as a positive control. A base sequence and an amino acid sequence of mGPR12 are shown in SEQ ID NOs: 7 and 8, respectively. A base sequence and an amino acid sequence of hMC3R are shown in SEQ ID NOs: 9 and 10, respectively.

As a result of the measurement, in both cases with Forskolin addition and without Forskolin addition, when making the mouse Nesfatin-1 act on mGPR12-transiently expressing HeLa cells, the increase in cAMP production was confirmed, and it was revealed that GPR12 is a receptor of Nesfatin-1.

Example 6

<Evaluation of cAMP Production in CHO-K1-cell Stable Expression System>

In Example 5, it was shown that the change of intracellular signals was measured in terms of the change in the cAMP concentration by transiently expressing GPR12 in HeLa cells, and then bringing Nesfatin-1 into contact with the cells. In the present Example, it was verified that the change of the intracellular signals was measured in terms of the change in the cAMP concentration by preparing CHO-K1 cells that express GPR12 stably by introducing a gene encoding GPR12. Further, as the test substance in the present Example, while Nesfatin-1 (82 amino acids) was used in Example 5, a mid-segment thereof, namely, Nesfatin-1M30 (SEQ ID NO: 11), was used for the examination. Furthermore, as an example of a modified peptide of Nesfatin-1 or Nesfatin-1M30, in the sequence of human Nesfatin-1M30 (Mid Segment), $M30_{13}$ Ag-A (SEQ ID NO: 50) that is a peptide prepared by substituting the all of amino acid sequences of the 11th (Leu) and the 13th to the 17th from the N-terminus with alanine (Ala), and M30_MSH-A (SEQ ID NO: 51) that is a peptide prepared by substituting all of amino acid sequences of the 22nd to 25th from the N-terminus with alanine were also used to examine the influence of the modified peptide on the change of cAMP concentration in cells.

The preparation of cells stably expressing GPR12 was conducted by a conventional method, and hereinafter described briefly. A vector (pcDNA3.1-GPR12) in which a gene (cDNA) encoding mouse GPR12 (SEQ ID NO: 8) was inserted at the downstream of a CMV promoter of pcDNA3.1 (TM) (Invitrogen Corporation) was prepared, 10 µg of the vector was mixed with 250 µL of medium OPTI-MEM™ (Invitrogen Corporation), and 10 µg of Lipofectamine™ 2000 Reagent (Invitrogen Corporation) was mixed with 250 µL of medium OPTI-MEM™, 5 minutes later both mixtures were mixed, and the resultant mixture was left over at room temperature for 20 minutes to prepare a transfection reagent. Chinese hamster ovary cells (CHO-K1) [ATCC Cat. No. CCl-61] plated onto a 6-well plate at $1.5\times10^6$ cells/well on the previous day in advance were washed with medium OPTI-MEM™ once, and the above-mentioned transfection reagent (vector and Lipofectamine™ 2000 Reagent) was added to the cells dropwise to perform transfection. The resultant transfected cells were incubated at 37° C. for 5 hours in a $CO_2$ incubator, and then the medium was replaced by Ham's F12 medium. Further, the next day the medium was exchanged with Ham's F12 medium containing 100 µg/mL of Geneticin® (Invitrogen Corporation), and furthermore the next day the medium was exchanged with the same medium containing 200 μg/mL of Geneticin®, and the following day the medium was exchanged with the same medium containing 700 μg/mL of Geneticin®, and after that, culturing was continued under the conditions of 37° C. and 5% $CO_2$ in a medium containing Geneticin® at the same concentration. Colonies of the cells were recovered 2 weeks after the transfection, plated onto a 10-cm dish again, cultured in Ham's F12 medium containing 700 μg/mL of Geneticin®, and the colonies were recovered, and then the CHO-K1 cells stably expressing GPR12 (CHO-K1-GPR12) were obtained.

A step of bringing a test substance into contact with the CHO-K1-GPR12 cells was conducted as follows. Cells were recovered from the confluent culture of the CHO-K1-GPR12 cells in a 10-cm dish, plated onto 10-cm dishes by dividing the culture in four quarters, and cultured for 2 days in Ham's F12 medium containing 700 μg/mL of Geneticin®. After removing the medium, the resultant culture cells were washed once with the medium containing no Geneticin®, and then cultured under the conditions of 37° C. for 30 minutes and 5% $CO_2$ in Ham's F12 medium containing $10^{-5}$ M of Forskolin but containing no test substance ((−) group), in the same medium containing $10^{-9}$ M of Nesfatin-1 M30 peptide and $10^{-5}$ M of Forskolin (Mid-segment group), in the same medium containing $10^{-9}$ M of M30_Ag-A peptide and $10^{-5}$ M of Forskolin (M30_Ag-A group), and in the same medium containing $10^{-9}$ M of M30_-MSH-A peptide and $10^{-5}$ M of Forskolin (M30_MSH-A group).

A step of measuring the intracellular cAMP was conducted by extracting cAMP with 95% ethanol from the cells brought into contact with the above-mentioned test substance using a method as described on pages 21 to 27 in volume 42 of Molecular and cellular Endocrinology by Hirayu et al. in 1985, and by measuring the cAMP level using a cyclic AMP Assay kit "YAMASA" (Yamasa Corporation, Catalog No. YSI-7701) in accordance with the protocol attached to the kit.

The measured intracellular cAMP level was evaluated in terms of a ratio (Fold) of each intracellular cAMP level with respect to the mean of the intracellular cAMP level in the (−) group that is set as unity, in which CHO-K1-GPR12 cells were cultured in the medium containing no peptide.

Figure 3:
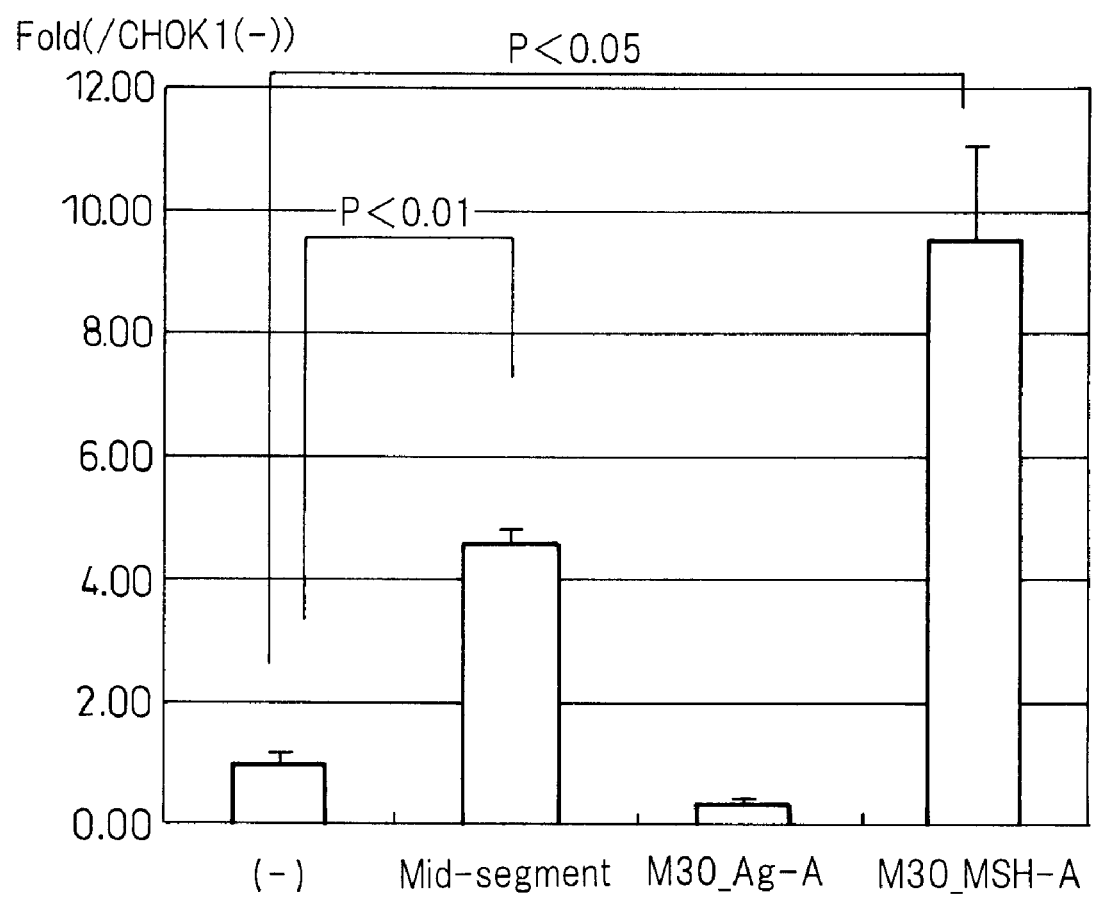
FIG. 3 is a bar graph showing the results comparing the cAMP production level in the presence of Forskolin for cells expressing mGPR12 stably (CHO-K1-GPR12). Mid-segment, M30_Ag-A and M30_MSH-A each represent CHO-K1-GPR12 cultured in a medium, to which Nesfatin-1M30 peptide, M30_Ag-A, and M30_MSH-A were added at a concentration of $10^{-9}$M, respectively. (−) represents CHO-K1-GPR12 cultured in a medium adding no test substance.

The values of the intracellular cAMP level in the CHO-K1 cells expressing GPR12 stably (CHO-K1-GPR12) brought into contact with Nesfatin-1M30 (Mid-segment), M30_Ag-A and M30_MSH-A are shown in FIG. 3 together with the intracellular cAMP level measured with the cells cultured in the medium containing no peptide (−).

The results of the measurement indicated that the intracellular cAMP level of the group (Mid-segment) in which Nesfatin-1M30 was brought into contact with CHO-K1-GPR12 was found to be elevated by about 5-fold compared with that of the group (−) cultured in the medium containing no peptide. From these results, it was found that, in addition to Nesfatin-1 in Example 5, Nesfatin-1M30 also induced intracellular signaling through GPR12. Further, from the results of M30_Ag-A and M30_MSH-A that are modified peptides of Nesfatin-1M30, it was shown that the intracellular cAMP level of the group of M30_Ag-A was hardly elevated while the level of the group (M30_MSH-A) in which M30_MSH-A was brought into contact with the cells was elevated about 10-fold compared with that of the group (−) cultured in the medium containing no peptide. As described above, since there is a difference in the cellular signal induction depending on the type of modified peptide, it has been shown that such a modified peptide or an analog of the modified peptide can be screened by using the cells expressing GPR12.

Example 7

<Evaluation of CREB Phosphorylation in CHO-K1-cell Stable Expression System>

As a typical signal transduction pathway after the elevation of intracellular cAMP level, there have been known a pathway such as activation of cAMP-dependent protein kinase A (PKA), phosphorylation of CRE-binding protein (CREB) by PKA, and increase in the expression of a gene cluster having cAMP response element (CRE) upstream thereof. Therefore, as an indicator of the measurement of cellular signal level, firstly the reaction by phosphorylation of CREB was studied to examine whether not only the change of the intracellular cAMP concentration but also the subsequent reaction of the signal transduction pathway is utilizable or not.

Using Nesfatin-1M30 (Mid-segment) as a test substance, the method for bringing the test substance into contact with cells was conducted as follows. The confluent CHO-K1 cells and CHO-K1-mGPR12 cells were recovered in 10-cm dishes, plated onto 10-cm dishes by dividing the cell colony in four quarters, and cultured for 2 days in Ham's F12 medium (as for CHO-K1-mGPR12, 700 μg/mL of Geneticin® was contained). After removing the medium, the resultant cultured cells were washed once with the medium containing no Geneticin®, and then Ham's F12 medium containing $10^{-9}$ M of Nesfatin-1M30 (Mid-segment) peptide was added to the cells. The medium containing the test substance was added, and then it was removed in 0 minute (without containing a test substance), 5 minutes, 15 minutes, 30 minutes and 60 minutes. The proteins were extracted from the cells using extraction buffer (1% Igepal CA-630, 0.5% sodium deoxycholate, 0.1% SDS, 1 mM DTT, 1 mM sodium orthovanadate, 100 μM PMSF in PBS(−)), and further, an aliquot (15 μL) of the resultant extracts were diluted with a sample treatment solution for SDS-PAGE (Daiichi Pure Chemicals Co., Ltd.), and the resultant sample was subjected to the detection by using a western blotting method. The western blotting was conducted in the following manner. SDS-gel electrophoresis was conducted by using the protein extracts from each cells; and then the protein was transcribed into Amersham hybond-P[198] (GE Healthcare); and using anti-phosphorylation CREB antibody (Cell Signaling Technology, Inc., Catalog No. #9191) for detecting the phosphorylated CREB, the phosphorylated CREB was detected with an ECL plus western blotting detection reagents (GE Healthcare) kit, in accordance with the attached protocol. Further, in order to prove that the CREB level contained in the protein extracts of the cells used is the same, using the same protein extracts as in the above, the detection was similarly conducted by a western blotting method using an antibody directed against CREB (also responses to the non-phosphorylated CREB) (Cell Signaling Technology, Inc., Catalog No. #9197). (FIG. 4A)

Further, the concentration dependence was examined by using Nesfatin-1M30 (Mid-segment: SEQ ID NO: 11). The concentrations used were $10^{-12}$ M, $10^{-11}$ M, $10^{-10}$ M and $10^{-9}$ M. Similarly to the above-described experiment, Nesfatin-1M30 in each concentration was brought into contact with CHO-K1-mGPR12 cells, and the resultant cells were incubated for 15 minutes. Subsequently, cellular proteins were extracted, and the phosphorylated CREB (p-CREB) was detected by a western blotting method. The results are shown in FIG. 4B.

Figure 4:
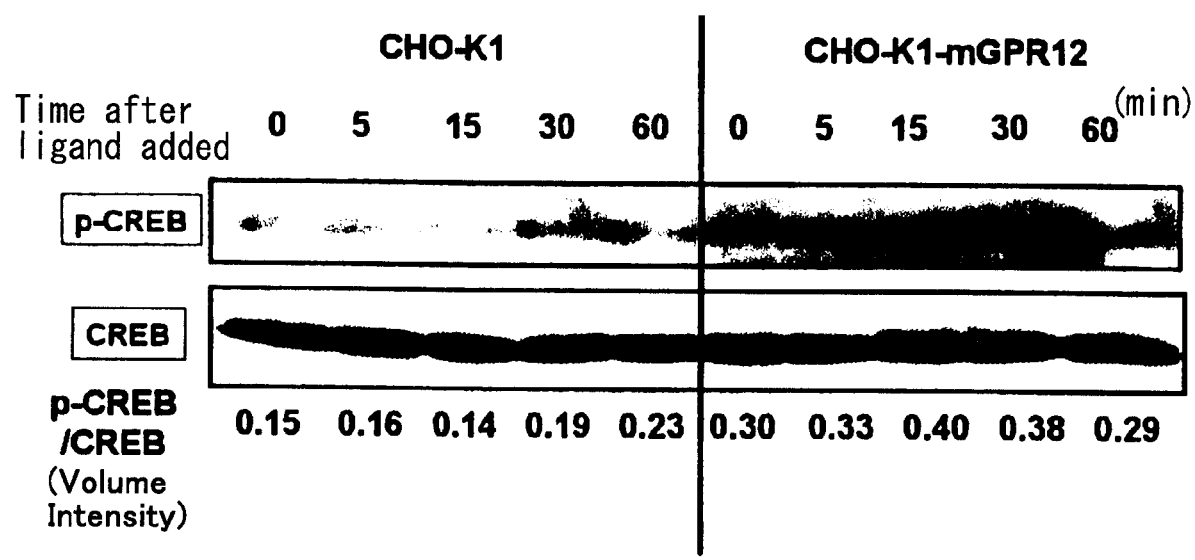
FIGS. 4A and 4B.
Figure 4:
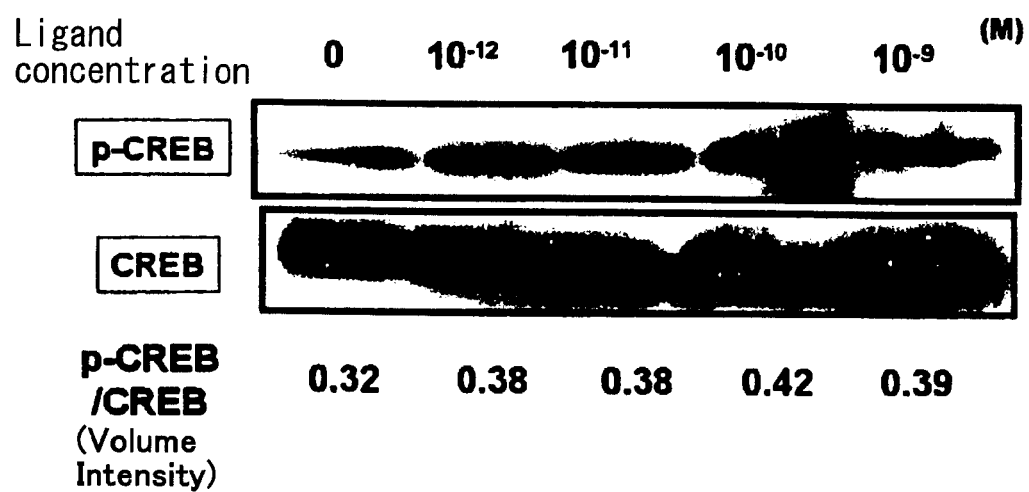

In FIG. 4A, 15 minutes or later after bringing Nesfatin-1M30 (Mid-segment) into contact with the cells, it was observed that the stained band of the phosphorylated CREB (p-CREB) was darker in the CHO-K1-mGPR12 cells, and as a result, it was shown that the phosphorylation of CREB was induced by Nesfatin-1 M30 (Mid-segment). Further, when the CREB per se was detected (CREB), since there was no difference in the concentration of the stained band at each time point, the total level of CREB contained in the protein extracts of the cells was not considered to be different.

Further, in FIG. 4B, it was found that the phosphorylation of CREB was enhanced depending on the M30 peptide concentration. From these, it has been shown that the detection of phosphorylation of CREB can also be used for the detection of the signals using cells expressing GPR12

Example 8

<Evaluation of Expression of a CRE-Reporter Gene in NB41A3 Cells Expressing GPR12 Endogenously>

In Example 7, as one of intracellular signals induced by the elevation of cAMP level, an actual example of the evaluation of Nesfatin-1M30 was explained by detecting signals using phosphorylation of CREB as an indicator. Signals associated with the elevation of cAMP level are said to be exemplified by the case where the phosphorylated CREB bonds to the site referred to CRE (cAMP responsive element) in the genome, which then activates the expression of a gene located downstream of CRE. Further, as a method for examining transcriptional activation by CRE, there is a method according to a reporter gene. By binding a reporter gene such as an enzyme (for example, luciferase and the like), a fluorescent protein (for example, GFP and the like) and others to the site downstream of CRE, the reporter gene in which the transcription is activated through CRE is expressed eventually as a protein having a function in the cell. The level of the transcriptional activation of CRE may be determined by measuring the enzyme activity, the fluorescence intensity and the like. For these reasons, an experiment was performed to examine whether the reaction of GPR12 and a Nesfatin-1 related peptide is measurable in a system using a CRE-reporter gene or not.

NB41A3 cells (ATCC-CCL147), a cell strain derived from mouse brain neuroblastoma, in which GPR12 was endogenously expressed were used. The confluent NB41A3 cells were recovered in a 10-cm dish, plated onto 10 cm-dishes after dividing the cell colony in four quarters, and cultured for one day in Ham's F12K medium. The cells were transfected with 5 µg of the reporter plasmid pCRE-Luc (Stratagene Corporation, Catalog No. 219074) in which TATA-BOX and luciferase were incorporated into downstream of CRE by a calcium phosphate method. The cells were washed with Ham's F12K medium 16 hours after the transfection. Ham's F12K medium containing no test substance (Vehicle), Ham's F12K medium containing $10^{-10}$ M of Nesfatin-1 M30 (Mid-Segment: SEQ ID NO: 11), Ham's F12K medium containing $10^{-10}$ M of a modified peptide M30_Ag-A (SEQ ID NO: 50) (M30_Ag-A), and Ham's F12K medium containing $10^{-10}$ M of a modified peptide M30_MSH-A (SEQ ID NO: 51) (Mid-Segment) were added to the cells, and the resultant mediums were cultured under the conditions of 37° C. and 5% $CO_2$ for 16 hours. After the culturing, the cells were washed twice with phosphate-buffered saline (PBS), lysed with 4 mL of lysis buffer (an aqueous solution containing 25 mM of glycylglicine (pH 7.8), 15 mM of magnesium sulfate, 4 mM of glycol ether diaminetetraacetic acid (EGTA), 1 mM of dithiothreitol (DTT), and 1% (volume/volume) of Triton X-100). Subsequently, 100 µL of the cell lysate was diluted with 350 µL of assay buffer (an aqueous solution containing 25 mM of glycylglicine (pH 7.8), 15 mM of magnesium sulfate, 4 mM of glycol ether diaminetetraacetic acid (EGTA), 16 mM of potassium dihydrogenphosphate, and 2 mM of adenosine triphosphate (ATP)). After adding 200 µL of 0.2 mM of d-luciferin to the diluted cell lysate, the luminescence was measured for 10 seconds by a luminometer, and the amount of luminescence (units) was determined. Further, the amount of protein in each cell lysate was measured by BCA™ Protein Assay Kit-Reducing Agent Compatible (Pearce, Catalog No. 23250), and the value obtained by dividing the amount of luminescence (units) by the amount of protein (µg) in a sample was determined as a luciferase activity. NB41A3 cells were transfected with a reporter plasmid (pCRE-Luc), and to the resultant transfected cells were added M30_Ag-A or M30_MSH-A at a concentration of $10^{-8}$ M, $10^{-9}$ M, $10^{-10}$ M, $10^{-11}$ M, $10^{-12}$ M and 0 M (containing no test substance), respectively. The cells were cultured for 16 hours, and then the level of luciferase activity was also determined.

Figure 5:
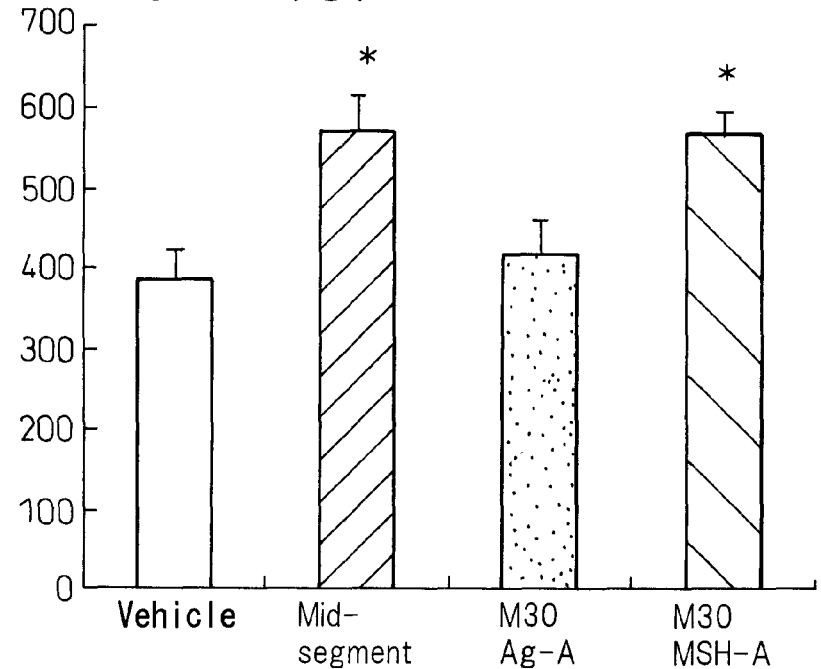
FIGS. 5A, 5B and 5C.
Figure 5:
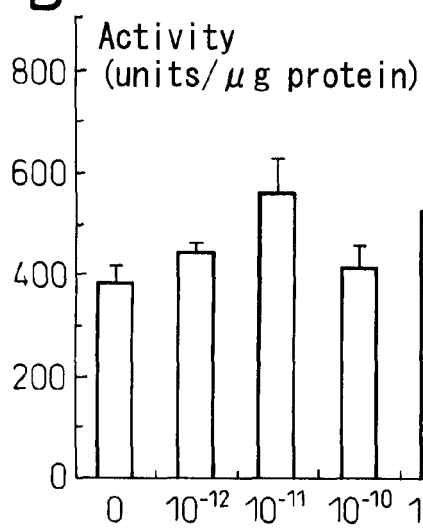
Figure 5:
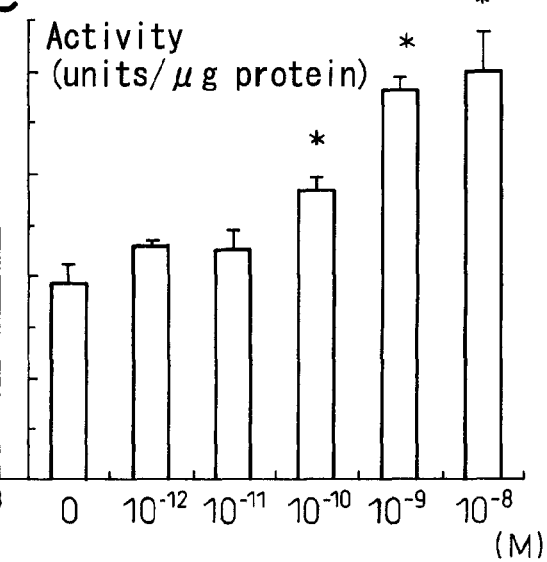

The level of luciferase activity in the resultant cells obtained after the NB41A3 cells transfected with a reporter plasmid (pCRE-Luc) were brought into contact with Nesfatin-M30 (Mid-segment), M30_Ag-A, and M30_MSH-A, respectively, at a concentration of $10^{-10}$ M for 16 hours are shown in FIG. 5A.

From the results shown in FIG. 5A, compared with the case (Vehicle) where a peptide was not brought into contact with the cells, in the case where Nesfatin-M30 (Mid-segment) and M30_MSH-A were brought into contact with the cells in which a reporter plasmid (a reporter gene) was introduced, the luciferase activity was found to be enhanced, while in the case where M30_MSH-A was brought into contact with the cells, the luciferase activity was not found to be different from that in the case of Vehicle at all. These results are similar to the change of the intracellular cAMP concentration in Example 6 and the phosphorylation of CREB in Example 7.

Further, the luciferase activity in the case where M30_Ag-A (FIG. 5B) or M30_MSH-A (FIG. 5C) at a concentration of $10^{-8}$ M, $10^{-9}$ M, $10^{-10}$ M, $10^{-11}$ M, $10^{-12}$ M and 0 M, respectively, were brought into contact with the cells in which NB41A3 cells were transfected with reporter plasmid pCRE-Luc for 16 hours are shown in FIGS. 5B and 5C.

When M30_Ag-A was brought into contact with the cells containing a reporter plasmid (a reporter gene) by varying the concentration of M30_Ag-A, the concentration-dependent enhancement of the luciferase activity was not found (FIG. 5B). On the other hand, when M30_MSH-A was brought into contact with the cells containing a reporter plasmid (a reporter gene) by varying the concentration of M30_MSH-A, the enhancement of the concentration-dependent luciferase activity was observed (FIG. 5C).

From these results, it has been shown that the detection of the expression of a gene located downstream of CRE can also be used for the detection of the signals using cells expressing GPR12.

Comparative Example 1

<Influence by Intraperitoneal Administration of a Nesfatin-1-modified Peptide on the Amount of Food Intake in a Mouse>

In Examples 6 to 8, the capability of evaluating the activity of a Nesfatin-1-related peptide was demonstrated by the detection of cellular signals in the cells expressing GPR12. On the other hand, International Publication Number WO2006/137597 discloses that the activity of Nesfatin was evaluated by examining the suppression of the amount of food intake or the suppression of weight gain of the animals administered with a Nesfatin-related peptide. Based on the above, an experiment was performed to examine whether the consistency is observed between the evaluation results by the cellular signals through GPR12 and those by animals or not.

A 7-week-old C57BL/6J strain male mouse (CLEA Japan, Inc.) was used as an experimental animal. After purchasing the mouse, the mouse was raised at 22° C. in cycles of the 12-hour light period from 6 a.m. to 6 p.m. and the 12-hour dark period from 6 p.m. to 6 a.m. on the next morning with free access to pelleted feed (CLEA Japan, Inc., CE-2).

A 5 nmol aliquot of Nesfatin-1M30 (Mid-segment, SEQ ID NO: 11), M30_Ag-A (SEQ ID NO: 50), or M30_MSH-A (SEQ ID NO: 51) was dissolved in each 100 μL of saline, and each of the resultant solutions was administered intraperitoneally to a C57BL/6J mouse at a dose of 0.25 nmol per gram of body weight of the mouse. In the control group, only saline (Vehicle) was administered. Each mouse (5 mice in each group) was intraperitoneally given a single injection of a sample using a tuberculin syringe with 26 G needle, immediately before the dark period (6 p.m.).

Each mouse administered was placed in an individual cage, and the amount of food intake was determined by measuring the decreased amount of the pelleted feed during the period from 0 to 3 hours after the administration of a test substance. In the mouse administered with each test sample, the amount of food intake during 3 hours after the administration (g/3 h) is shown in FIG. 6.

Figure 6:
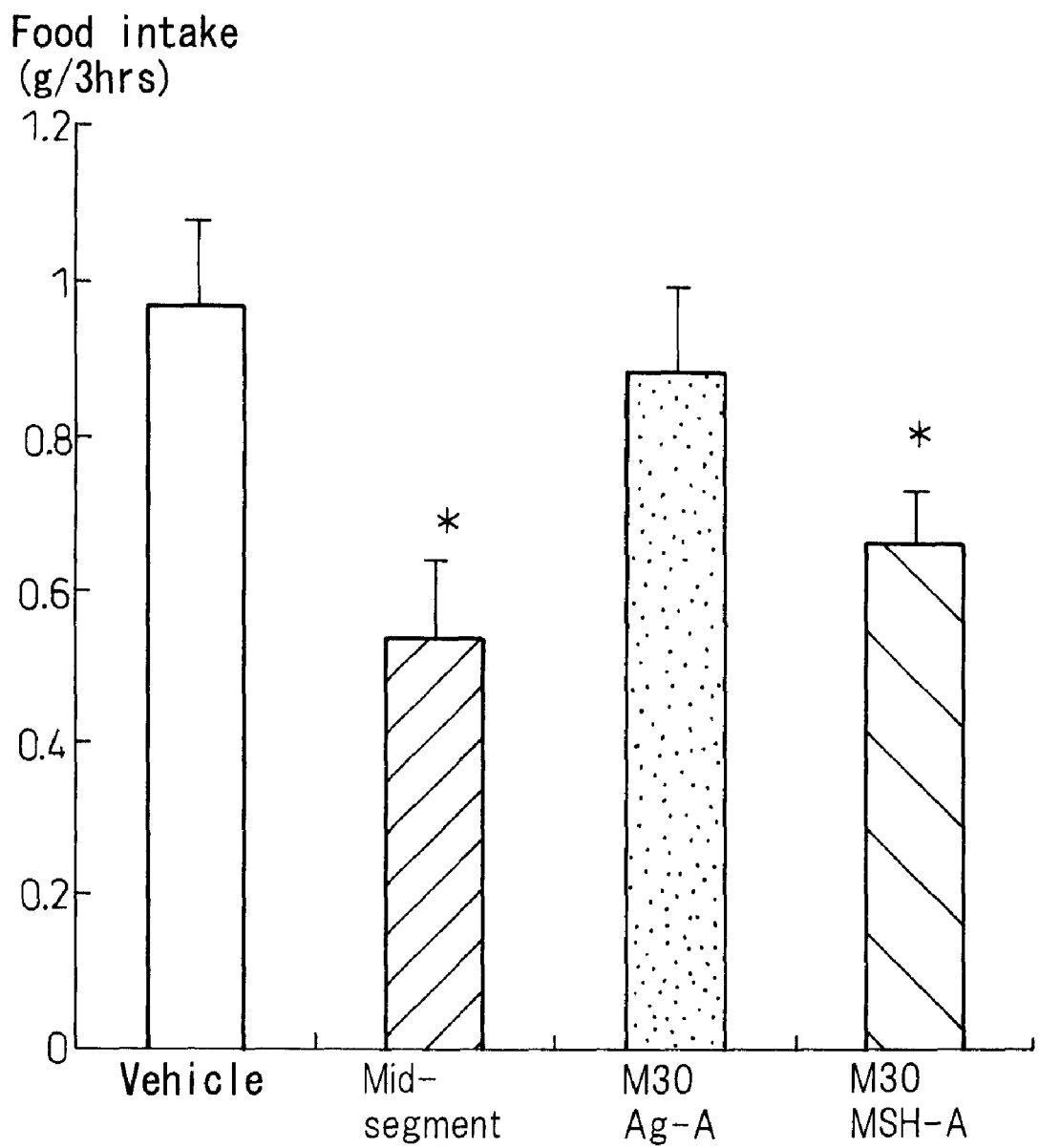
FIG. 6 is a bar graph showing the amount (g/3 hr) of food intake at 3 hours after administering each test substance in a mouse administered intraperitoneally with saline (Vehicle), Nesfatin-1M30 (Mid-segment), M30_Ag-A or M30_MSH-A.

As shown in FIG. 6, in the mouse administered with Nesfatin-1M30 (Mid-segment) and M30_MSH-A, a significant decrease of the food intake was observed compared with that in the control group (Vehicle). On the other hand, no difference was observed in the amount of food intake between the mouse administered with M30_Ag-A and that of the control group.

The results of Comparative Example 1, namely, that suppression in the food intake was not recognized in the mouse administered with M30_Ag-A, leads to the discussion similar to that revealed in Examples 6 to 8, namely, that the reaction was observed in the cellular signals through GPR12 in M30_MSH-A. From the above, it has been shown that the evaluation of Nesfatin-1 action by cellular signals using GPR12 reflects the Nesfatin-1 activities (food intake suppression, body-weight gain suppression) in animals.

From these results, it has been shown that Nesfatin-1-related substances (a Nesfatin-1-like action substance and a Nesfatin-1-action regulating substance) can be screened based on the cellular signals associated with GPR12.

Industrial Applicability

The present invention provides a method for screening a Nesfatin-1-action regulating substance or a Nesfatin-1-like action substance in vitro or in silico. Further, a Nesfatin-1-action regulating substance or Nesfatin-1-like action substance obtained according to the present invention is expected as a therapeutic agent of a disease such as obesity syndrome, eating disorder, dysbolism, diabetes mellitus, autoimmune disease, rheumatoid arthritis (RA), chronic obstructive pulmonary disease (COPD), and the like.

Explanation of Sequence Listings (1) SEQ ID NO: 1: an amino acid sequence of human-derived Nesfatin-1
(2) SEQ ID NO: 2: an amino acid sequence of mouse-derived Nesfatin-1
(3) SEQ ID NO: 3: an amino acid sequence of rat-derived Nesfatin-1
(4) SEQ ID NO: 4: a base sequence of human-derived Nesfatin-1
(5) SEQ ID NO: 5: a base sequence of mouse-derived Nesfatin-1
(6) SEQ ID NO: 6: a base sequence of rat-derived Nesfatin-1
(7) SEQ ID NO: 7: a base sequence of mouse-derived GPR12 and an amino acid sequence of the CDS
(8) SEQ ID NO: 8: an amino acid sequence of CDS of mouse-derived GPR12
(9) SEQ ID NO: 9: a base sequence of human-derived MC3R and an amino acid sequence of the CDS
(10) SEQ ID NO: 10: an amino acid sequence of CDS of human-derived MC3R
(11) SEQ ID NO: 11: an amino acid sequence of human-derived Nesfatin-1M30
(12) SEQ ID NO: 12: an amino acid sequence of rat-derived Nesfatin-1M30
(13) SEQ ID NO: 13: an amino acid sequence of mouse-derived Nesfatin-1M30
(14) SEQ ID NO: 14: an amino acid sequence of human-derived Nesfatin-1M16
(15) SEQ ID NO: 15: an amino acid sequence of human-derived Nesfatin-1M14
(16) SEQ ID NO: 16: an amino acid sequence of human-derived Nesfatin-1M10M
(17) SEQ ID NO: 17: an amino acid sequence of rat-derived Nesfatin-1M16
(18) SEQ ID NO: 18: an amino acid sequence of rat-derived Nesfatin-1M14
(19) SEQ ID NO: 19: an amino acid sequence of rat-derived Nesfatin-1M10M
(20) SEQ ID NO: 20: an amino acid sequence of mouse-derived Nesfatin-1M16
(21) SEQ ID NO: 21: an amino acid sequence of mouse-derived Nesfatin-1M14
(22) SEQ ID NO: 22: an amino acid sequence of mouse-derived Nesfatin-1M10M
(23) SEQ ID NO: 23: an amino acid sequence of human-derived NUCB1-1
(24) SEQ ID NO: 24: an amino acid sequence of rat-derived NUCB1-1
(25) SEQ ID NO: 25: an amino acid sequence of mouse-derived NUCB1-1
(26) SEQ ID NO: 26: an amino acid sequence of human-derived NUCB1-M30
(27) SEQ ID NO: 27: an amino acid sequence of rat-derived NUCB1-M30
(28) SEQ ID NO: 28: an amino acid sequence of mouse-derived NUCB1-M30
(29) SEQ ID NO: 29: an amino acid sequence of human-derived NUCB1-M16
(30) SEQ ID NO: 30: an amino acid sequence of human-derived NUCB1-M14
(31) SEQ ID NO: 31: an amino acid sequence of human-derived NUCB1-M10M
(32) SEQ ID NO: 32: an amino acid sequence of rat-derived NUCB1-M16
(33) SEQ ID NO: 33: an amino acid sequence of rat-derived NUCB1-M14
(34) SEQ ID NO: 34: an amino acid sequence of rat-derived NUCB1-M10M
(35) SEQ ID NO: 35: an amino acid sequence of mouse-derived NUCB1-M16
(36) SEQ ID NO: 36: an amino acid sequence of mouse-derived NUCB1-M14
(37) SEQ ID NO: 37: an amino acid sequence of mouse-derived NUCB1-M10M
(38) SEQ ID NO: 38: NESFATIN-1 1stPCR Primer mNucB2-F337
(39) SEQ ID NO: 39: NESFATIN-1 1stPCR Primer mNucB2-R712

(40) SEQ ID NO: 40: NESFATIN-1 2ndPCR Primer mNucB2-N3
(41) SEQ ID NO: 41: NESFATIN-1 2ndPCR Primer mNucB2-R589
(42) SEQ ID NO: 42: an amino acid sequence of human-derived NESFATIN
(43) SEQ ID NO: 43: an amino acid sequence of human-derived NESFATIN (Mature)
(44) SEQ ID NO: 44: an amino acid sequence of mouse-derived NESFATIN
(45) SEQ ID NO: 45: an amino acid sequence of mouse-derived NESFATIN (Mature)
(46) SEQ ID NO: 46: an amino acid sequence of rat-derived NESFATIN
(47) SEQ ID NO: 47: an amino acid sequence of rat-derived NESFATIN (Mature)
(48) SEQ ID NO: 48: an amino acid sequence of CDS of mouse-derived GPR3
(49) SEQ ID NO: 49: an amino acid sequence of CDS of mouse-derived GPR6
(50) SEQ ID NO: 50: an amino acid sequence of a modified peptide (M30$_{13}$ Ag-A) of human-derived Nesfatin-1M30
(51) SEQ ID NO: 51: an amino acid sequence of a modified peptide (M30_MSH-A) of human-derived Nesfatin-1M30

The invention claimed is:

1. A method for screening for a substance that has Nesfatin-1-like action, said method comprising:

contacting isolated cells with a test substance, wherein the isolated cells express GPR12; and identifying that the test substance is a substance that has Nesfatin-1-like action when the test substance binds with the receptor or activates the signal transduction ability of the receptor;

wherein Nesfatin-1-like action is an action for suppressing food intake and/or body weight gain.

2. The screening method according to claim 1, wherein the test substance is a peptide or a peptide analog obtained by modifying a peptide having the amino acid sequence represented by any of SEQ ID NOs: 1 to 3 or 11 to 37.

3. A method for screening for a substance that regulates Nesfatin-1 action, said method comprising:

contacting isolated cells with a test substance in the presence of Nesfatin-1, wherein the isolated cells express GPR12; and identifying a test substance that regulates Nesfatin-1 action based on a change of the binding capacity of Nesfatin-1 with the receptor, or a change of the signal transduction ability of the receptor;

wherein when the test substance inhibits the binding between Nesfatin-1 and the receptor, or decreases the intensity or frequency of the signal transduction, the test substance is identified as a substance inhibiting Nesfatin-1 action, and wherein when the test substance facilitates the binding between Nesfatin-1 and the receptor, or increases the intensity or frequency of the signal transduction, the test substance is identified as a substance facilitating Nesfatin-1 action;

wherein Nesfatin-1-like action is an action for suppressing food intake and/or body weight gain.

* * * * *